(12) United States Patent
Wilson et al.

(10) Patent No.: US 12,070,516 B2
(45) Date of Patent: Aug. 27, 2024

(54) HAIR STYLING COMPOSITIONS

(71) Applicant: L'OREAL, Paris (FR)

(72) Inventors: Liam Wilson, Westfield, NJ (US); Heather Lee, Kinnelon, NJ (US); Jun Liang, Staten Island, NY (US)

(73) Assignee: L'OREAL, Paris (FR)

( * ) Notice: Subject to any disclaimer, the term of this patent is extended or adjusted under 35 U.S.C. 154(b) by 0 days.

(21) Appl. No.: 18/064,470

(22) Filed: Dec. 12, 2022

(65) Prior Publication Data
US 2024/0197597 A1 Jun. 20, 2024

(51) Int. Cl.
A61K 8/42 (2006.01)
A61K 8/36 (2006.01)
A61K 8/37 (2006.01)
A61K 8/92 (2006.01)
A61Q 5/06 (2006.01)

(52) U.S. Cl.
CPC ............... *A61K 8/42* (2013.01); *A61K 8/361* (2013.01); *A61K 8/37* (2013.01); *A61K 8/92* (2013.01); *A61Q 5/06* (2013.01)

(58) Field of Classification Search
CPC . A61K 8/42; A61K 8/361; A61K 8/37; A61K 8/92; A61Q 5/06
See application file for complete search history.

(56) References Cited

U.S. PATENT DOCUMENTS

| | | | |
|---|---|---|---|
| 6,797,683 B2 | 9/2004 | Shana'a et al. | |
| 9,074,305 B2 | 7/2015 | Glenn, Jr. et al. | |
| 9,987,215 B2 | 6/2018 | Nogueira et al. | |
| 11,446,220 B2 | 9/2022 | Wang et al. | |
| 2003/0180246 A1* | 9/2003 | Frantz | C11D 1/652 424/70.21 |
| 2007/0048243 A1 | 3/2007 | Hansenne et al. | |
| 2008/0031908 A1 | 2/2008 | Aubrun-Sonneville et al. | |
| 2008/0280797 A1 | 11/2008 | Compain | |
| 2008/0311066 A1 | 12/2008 | Samain et al. | |
| 2013/0129654 A1 | 5/2013 | Litvin et al. | |
| 2014/0261517 A1* | 9/2014 | Humphreys | A61K 8/19 132/204 |
| 2016/0151272 A1 | 6/2016 | Alves et al. | |
| 2017/0319453 A1 | 11/2017 | Ando | |
| 2018/0214355 A1 | 8/2018 | Crane et al. | |
| 2018/0280267 A1 | 10/2018 | Rughani et al. | |
| 2018/0280269 A1 | 10/2018 | Rughani et al. | |
| 2018/0280270 A1 | 10/2018 | Rughani et al. | |
| 2018/0280271 A1 | 10/2018 | Fack et al. | |
| 2018/0311138 A1 | 11/2018 | Huynh et al. | |
| 2018/0353401 A1* | 12/2018 | Wossene | A61K 8/8152 |
| 2019/0000732 A1 | 1/2019 | Wang et al. | |
| 2019/0029949 A1 | 1/2019 | Ceballos et al. | |
| 2019/0142706 A1 | 5/2019 | Sverdlove et al. | |
| 2019/0201309 A1 | 7/2019 | Machover et al. | |
| 2019/0269602 A1* | 9/2019 | Fuchs | A61K 8/8152 |
| 2021/0030636 A1 | 2/2021 | Hsieh et al. | |
| 2021/0196600 A1 | 7/2021 | Shi et al. | |
| 2021/0196606 A1 | 7/2021 | Shi et al. | |
| 2021/0378941 A1* | 12/2021 | Coulombel | A61Q 5/06 |
| 2021/0386650 A1 | 12/2021 | Liard et al. | |
| 2021/0393505 A1 | 12/2021 | Liard et al. | |

FOREIGN PATENT DOCUMENTS

| | | | |
|---|---|---|---|
| BR | 112014009501 A2 | 5/2017 | |
| EP | 2066284 A1 | 6/2009 | |
| ES | 2796742 T3 | 11/2020 | |
| JP | 6346319 B2 | 6/2018 | |
| KR | 101328408 B1 | 11/2013 | |
| WO | WO-2016158012 A1 * | 10/2016 | ............... A61K 8/31 |
| WO | 2020242787 A1 | 12/2020 | |

OTHER PUBLICATIONS

Preliminary Search Report and Written Opinion issued on Aug. 14, 2023 for corresponding French Application No. FR 2301085.
Database GNPD [Online]; Mintel; Anonymous: "Argan Love Your Lips Hydrating Lipstick," 2013 XP093073231.

* cited by examiner

*Primary Examiner* — Lezah Roberts
*Assistant Examiner* — Abdulrahman Abbas
(74) *Attorney, Agent, or Firm* — POLSINELLI PC

(57) ABSTRACT

The present disclosure relates to hair styling compositions that exhibit non-Newtonian shear thinning behavior during use. The hair styling composition include: (a) one or more fatty amides, fatty alkanolamides, and/or alkoxylated fatty amides; (b) one or more non-hydroxy substituted fatty acids; (c) one or more hydroxy substituted fatty acids; (d) at least 70 wt. % of one or more low-polar oils; and less than 2 wt. % of water. Additional components such as, for example, alkoxylated polyol esters, water-soluble organic solvents, and other miscellaneous ingredients, can optionally be included in the hair styling compositions. The hair styling compositions are particularly useful for styling or shaping hair and for providing hold, discipline, and texture to hair.

19 Claims, No Drawings

HAIR STYLING COMPOSITIONS

FIELD OF THE DISCLOSURE

The present disclosure relates to hair styling compositions that exhibit non-Newtonian shear thinning behavior providing a solid-to-liquid transformation during use for easy application, while maintaining the styling attributes of a traditional styling solid (e.g., wax, clay, paste, pomade). The hair styling compositions are useful for styling or shaping the hair and for providing hold, discipline, and texture to the hair.

BACKGROUND

Consumers desire new multi-functional hair products that can not only impart good styling benefits to hair, but also simplify their routine by providing easier mechanisms of application and distribution onto the hair. Such products should be pleasing to the senses, have innovative, interesting and/or pleasing textures, without loss in functional performance. Furthermore, many consumers prefer hair products that are light in texture, easy to apply, and provide discipline/hold to the hair. Traditional hair styling products on the cosmetic market appear in various forms. They range anywhere from solutions, foams, gels, creams, waxes, mousses, sprays, serums, to aerosols and can impart a variety of levels of protection and style to the hair depending on the state of the hair and the components of the product. Generally, products that are designed to impart styling or shaping benefits to hair are in the form of hair styling or hair care/hair treatment products. Such products are sometimes solids, or very thick/viscous, making them difficult to apply. Upon application, these products may dry unevenly due to the product format or become stiff and/or "crunchy" with limited hold (i.e. the film is overly hard and brittle), which is undesirable for many consumers.

Current products for imparting styling or shaping benefits to hair often include water soluble film-forming polymers. Depending on the chemical make-up of these polymers, they may be either soluble in water, or they may be water insoluble polymers which are made water soluble via various chemical modifications, such as neutralization. Solutions comprising these polymers tend to be viscous, i.e., as the concentration of the polymer increases, its viscosity builds up rapidly. Translated to styling applications, as the solvent evaporates, the polymer solution becomes thicker on the hair surface, resulting in a sticky or tacky film.

SUMMARY OF THE DISCLOSURE

The instant disclosure relates to hair styling compositions having unique rheological properties. For instance, in various embodiments, the hair styling compositions exhibit non-Newtonian shear thinning behavior during use. The viscosity decreases as a function of shear stress applied to the composition. Therefore, at rest or when the compositions are subjected to very little physical manipulation, the compositions are more "solid-like," having the consistency of a wax. When the compositions are subjected to more vigorous physical manipulation, for example, when rubbed in the hand of a consumer and applied to the hair, the compositions become more "liquid-like." In other words, the compositions exhibit a solid-to-liquid transformation during use, which allow for ease of application. The hair styling compositions are particularly useful for providing the unique benefits solid styling products offer (such as clays and pastes), while being very easy to apply due to their distinctive rheology. For example, the compositions maintain the shape of hair, provide durable hold, and impart a pleasant texture and feel to hair, while being easy to apply due to their liquid-to-solid transformative behavior during use.

The hair styling compositions include:
(a) one or more fatty amides, fatty alkanolamides, and/or alkoxylated fatty amides;
(b) one or more non-hydroxy substituted fatty acids;
(c) one or more hydroxy substituted fatty acids;
(d) at least 70 wt. % of one or more low-polar oils; and
wherein the composition comprises less than 2 wt. % of water, and
all weight percentages are based on a total weight of the composition.

While not wishing to be bound by any particular theory, the inventors believe that the unique non-Newtonian shear thinning behavior of the compositions is due in part to combination of the (a) one or more fatty amides, fatty alkanolamides, and/or alkoxylated fatty amides and the and (c) one or more hydroxy substituted fatty acids, especially in combination with the (b) one or more non-hydroxy substituted fatty acids in low-polar oil medium. Without wishing to be bound by any particular theory, it is believed that the non-Newtonian shear thinning behavior results from hydrogen bonding between (c) hydroxy substituted fatty acid and itself and/or with the (a) one or more fatty amides, fatty alkanolamides, and/or alkolyated fatty amides. This occurs when the concentration of water is low such that it will not interfere with the hydrogen bonding mechanism. Hence, the use of a low-polar oil medium.

Non-limiting examples of fatty amides include fatty alkanolamides such as fatty acid alkanolamides including oleic acid diethanolamide, myristic acid monoethanolamide, soya fatty acids diethanolamide, stearic acid ethanolamide, oleic acid monoisopropanolamide, linoleic acid diethanolamide, stearic acid monoethanolamide (Stearamide MEA), behenic acid monoethanolamide, isostearic acid monoisopropanolamide (isostearamide MIPA), erucic acid diethanolamide, ricinoleic acid monoethanolamide, coconut fatty acid monoisopropanolamide (cocoamide MIPA), coconut acid monoethanolamide (Cocamide MEA), palm kernel fatty acid diethanolamide, coconut fatty acid diethanolamide, lauric diethanolamide, polyoxyethylene coconut fatty acid monoethanolamide, coconut fatty acid monoethanolamide, lauric monoethanolamide, lauric monoisopropanolamide (lauramide MIPA), myristic acid monoisopropanolamide (Myristamide MIPA), coconut fatty acid diisopropanolamide (cocamide DIPA), and mixtures thereof. In a preferred embodiment, the fatty acid alkanolamides are selected from cocamide MIPA, cocamide DEA, cocamide MEA, cocamide DIPA, and mixtures thereof.

Nonlimiting examples of non-hydroxy substituted fatty acids include lauric acid, palmitic acid, stearic acid, behenic acid, arichidonic acid, oleic acid, isostearic acid, sebacic acid, and a mixture thereof. In various embodiments, the non-hydroxy substituted fatty acid is selected from oleic acid, lauric acid, palmitic acid, myristic acid, stearic acid, linoleic acid, capric acid, and a combination thereof.

Nonlimiting examples of hydroxy substituted fatty acids include 12-hydroxystearic acid, 9,10-dihydroxyoctadecanoic acid, 9,10,18-trihydroxyoctadecanoic acid, lesquerolic acid, 15-hydroxyhexadecanoic acid, isoricinoleic acid, densipolic acid, 14-hydroxy-eicosa-cis-11-cis-17-dienoic acid, 2-hydroxyoleic acid, 2-hydroxylinoleic acid, 18-hydroxystearic acid, 15-hydroxylinoleic acid, and a combination thereof. Nonlimiting examples of low-polar oils include low-polar hydrocarbon oils, low-polar silicone oils, and mixtures thereof. In various embodiments, the one or more low-polar oils include low-polar hydrocarbon oils that are linear or branched hydrocarbons containing at least 20 carbon atoms, such as paraffinic hydrocarbons and olefins. Nonlimiting examples include C24-28 olefins, C30-45 olefins, C20-40 isoparaffins, hydrogenated polyisobutene, polyisobutene, polydecene, hydrogenated polydecene, mineral oil, petrolatum, pentahydrosqualene, squalene, squalane, and mixtures thereof. In preferred embodiments, the low-polar oils include one or more natural oil, in particular a vegetable oil. Nonlimiting examples of vegetable oils include: sunflower oil, canola oil, soybean oil, corn oil, peanut oil, palm oil, castor bean oil, cotton oil, lesquerella oil, crambe oil, safflower oil, and mixtures thereof.

The hair styling compositions optionally include one or more alkoxylated polyol esters. Nonlimiting examples of alkoxylated polyol esters include pegylated derivatives of propylene glycol oleate, propylene glycol caprylate/caprate, propylene glycol cocoate, propylene glycol stearate, and a mixture thereof. In some instances, the alkoxylated polyol esters are chosen from PEG-55 propylene glycol oleate, PEG-6 propylene glycol caprylate/caprate, PEG-8 propylene glycol cocoate, PEG-25 propylene glycol stearate, and PEG-120 propylene glycol stearate, and a mixture thereof. In a preferred embodiment, the one or more alkoxylated polyol esters are selected from PEG-55 propylene glycol oleate, PEG-6 propylene glycol caprylate/caprate, PEG-8 propylene glycol cocoate, PEG-25 propylene glycol stearate, and PEG-120 propylene glycol stearate, and a mixture thereof.

The hair styling compositions optionally include one or more water-soluble organic solvents. Non-limiting examples of water-soluble organic solvents include, for example, organic solvents selected from glycerin, alcohols (for example, C1-12, C1-10, C1-8, or C1-4 alcohols), polyols (polyhydric alcohols), glycols, and a mixture thereof. Non-limiting examples of monoalcohols and polyols include ethyl alcohol, isopropyl alcohol, propyl alcohol, benzyl alcohol, and phenylethyl alcohol, or glycols or glycol ethers such as, for example, monomethyl, monoethyl and monobutyl ethers of ethylene glycol, propylene glycol or ethers thereof such as, for example, monomethyl ether of propylene glycol, butylene glycol, hexylene glycol, dipropylene glycol as well as alkyl ethers of diethylene glycol, for example monoethyl ether or monobutyl ether of diethylene glycol. Other suitable examples of organic solvents are ethylene glycol, propylene glycol, butylene glycol, hexylene glycol, propane diol, and glycerin.

Additional components may optionally be included in the hair styling compositions, for example, additional fatty compounds (such as solid fatty compounds, e.g., waxes), film-forming polymers, thickening agents, cationic polymers, surfactants (anionic, cationic, amphoteric, nonionic), etc. In various embodiments, the hair styling compositions include one or more miscellaneous ingredients. Non-limiting examples of miscellaneous ingredients include preservatives, fragrances, pH adjusters, salts, buffers, antioxidants, flavonoids, vitamins, botanical extracts, UV filtering agents, proteins, protein hydrolysates and/or isolates, hydrotropes, pearlescent agents, fillers, composition colorants, humectants, etc.

The hair styling compositions are useful in various methods for treating hair, for example, human hair, including human hair of an individual's head. For example, the compositions are useful for: (i) improving or retaining curl definition or hold of hair; (ii) styling and shaping the hair; (iii) providing hair fiber alignment and discipline; and (iv) improving the appearance of hair; wherein the methods comprise applying a hair styling composition disclosed herein to the hair and styling the hair.

DETAILED DESCRIPTION OF THE DISCLOSURE

The instant disclosure relates to hair styling compositions and to methods of using the hair styling compositions to style hair. In various embodiments, the hair styling compositions exhibit non-Newtonian shear thinning behavior. Classical "Newtonian" fluids, as generally used herein, demonstrate a viscosity which is essentially independent of shear rate. "Non-Newtonian fluids," however, demonstrate a viscosity which either decreases or increases with increasing shear rate, e.g., the fluids are "shear thinning" or "shear thickening", respectively.

An example of a non-Newtonian fluid is a suspension of starch (flour) in water, sometimes called oobleck. Another non-Newtonian fluid is SILLY PUTTY, which is an example of a polymer based suspension. The application of force to some types of non-Newtonian fluids—for example by stabbing the surface with a finger, or rapidly inverting the container holding it-leads to the fluid behaving like a solid, rather than a liquid. Such non-Newtonian fluid is referred to as having a "shear thickening" property. More gentle treatment, such as slowly inserting a spoon, will leave it in its liquid state. Quickly pulling the spoon back out, however, triggers the return of the temporary solid state. Materials exhibiting such properties may be referred to as viscoelastic non-Newtonian fluids having shear thickening behavior. Non-Newtonian fluids, especially of multi-phase nature (foams, emulsions, dispersions and suspensions, slurries, for instance) and polymeric melts and solutions do not conform to the Newtonian postulate of the linear relationship between shear stress and shear rate in simple shear. Likewise, the apparent viscosity, defined as shear stress/shear rate, is not constant and is a function of shear stress or shear rate.

The viscosity of the hair styling compositions can be determined according to known methods for measuring viscosity. For instance, the viscosity is measured with a Discovery HR-2 rheometer from TA Instruments at 25°C using 40 mm parallel sand blasted plates, a 300 μm gap, and a shear range from 0.1/s to 100/s.

The hair styling compositions of the instant disclosure typically include:
(a) one or more fatty amides, fatty alkanolamides, and/or alkoxylated fatty amides;
(b) one or more non-hydroxy substituted fatty acids;
(c) one or more hydroxy substituted fatty acids;
(d) at least 70 wt. % of one or more low-polar oils;
(e) optionally, one or more alkoxylated polyol esters;
(f) optionally, about 0.1 to about 10 wt. % of one or more water-soluble organic solvents; and/or
(g) optionally, about 0.1 to about 8 wt. % of one or more miscellaneous ingredients;
wherein the composition comprises less than 2 wt. % of water, and
all weight percentages are based on a total weight of the composition.
wherein the hair styling composition exhibits non-Newtonian shear thickening behavior.

(a) Fatty Amides, Fatty Alkanolamides, and/or Fatty Alkoxylated Amides

Non-limiting examples of fatty amides include fatty alkanolamides such as fatty acid alkanolamides. The fatty acid alkanolamides may be fatty acid monoalkanolamides or fatty acid dialkanolamides or fatty acid isoalkanolamides, and may have a $C_{2-8}$ hydroxyalkyl group (the $C_{2-8}$ chain can be substituted with one or more than one —OH group). Non-limiting examples include fatty acid diethanolamides (DEA) or fatty acid monoethanolamides (MEA), fatty acid monoisopropanolamides (MIPA), fatty acid diisopropanolamides (DIPA), and fatty acid glucamides (acyl glucamides).

Suitable fatty acid alkanolamides include those formed by reacting an alkanolamine and a C6-C36 fatty acid. Examples thereof include, but are not limited to: oleic acid diethanolamide, myristic acid monoethanolamide, soya fatty acids diethanolamide, stearic acid ethanolamide, oleic acid monoisopropanolamide, linoleic acid diethanolamide, stearic acid monoethanolamide (Stearamide MEA), behenic acid monoethanolamide, isostearic acid monoisopropanolamide (isostearamide MIPA), erucic acid diethanolamide, ricinoleic acid monoethanolamide, coconut fatty acid monoisopropanolamide (cocoamide MIPA), coconut acid monoethanolamide (Cocamide MEA), palm kernel fatty acid diethanolamide, coconut fatty acid diethanolamide, lauric diethanolamide, polyoxyethylene coconut fatty acid monoethanolamide, coconut fatty acid monoethanolamide, lauric monoethanolamide, lauric acid monoisopropanolamide (lauramide MIPA), myristic acid monoisopropanolamide (Myristamide MIPA), coconut fatty acid diisopropanolamide (cocamide DIPA), and mixtures thereof.

In an embodiment, the fatty acid alkanolamides include cocamide MIPA, cocamide DEA, cocamide MEA, cocamide DIPA, and mixtures thereof.

In an embodiment, the fatty acid alkanolamides is selected from cocamide MIPA commercially available under the tradename EMPILAN from Innospec Active Chemicals.

Additional non-limiting examples of fatty acid alkanolamides include oleic acid diethanolamide, myristic acid monoethanolamide, soya fatty acids diethanolamide, stearic acid ethanolamide, oleic acid monoisopropanolamide, linoleic acid diethanolamide, stearic acid monoethanolamide (Stearamide MEA), behenic acid monoethanolamide, isostearic acid monoisopropanolamide (isostearamide MIPA), erucic acid diethanolamide, ricinoleic acid monoethanolamide, coconut fatty acid monoisopropanolamide (cocoamide MIPA), coconut acid monoethanolamide (Cocamide MEA), palm kernel fatty acid diethanolamide, coconut fatty acid diethanolamide, lauric diethanolamide, polyoxyethylene coconut fatty acid monoethanolamide, coconut fatty acid monoethanolamide, lauric monoethanolamide, lauric acid monoisopropanolamide (lauramide MIPA), myristic acid monoisopropanolamide (Myristamide MIPA), coconut fatty acid diisopropanolamide (cocamide DIPA), and mixtures thereof.

Fatty acid alkanolamides include those of the following structure:

wherein $R_4$ is an alkyl chain of 4 to 20 carbon atoms ($R_4$ may be, for example, selected from lauric acid, coconut acid, palmitic acid, myristic acid, behenic acid, babassu fatty acid, isostearic acid, stearic acid, corn fatty acid, soy fatty acid, shea butter fatty acids, caprylic acid, capric acid, and mixtures thereof);

$R_5$ is selected from —$CH_2OH$, —$CH_2CH_2OH$, —$CH_2CH_2CH_2OH$, —$CH_2(CHOH)_4CH_2OH$, -benzyl, and mixtures thereof;

$R_6$ is selected from —H, —$CH_3$, —$CH_2OH$, —$CH_2CH_3$, —$CH_2CH_2OH$, —$CH_2CH_2CH_2OH$, —$CH_2(CHOH)_4CH_2OH$, -benzyl, and mixtures thereof.

In some embodiments, the one or more of the fatty acid alkanolamides are preferably acyl glucamides, for example, acyl glucamides having a carbon chain length of 8 to 20. Non-limiting examples include lauroyl/myristoyl methyl glucamide, capryloyl/capryl methyl glucamide, lauroyl methyl glucamide, myristoyl methyl glucamide, capryloyl methyl glucamide, capryl methyl glucamide, cocoyl methyl glucamide, capryloyl/caproyl methyl glucamide, cocoyl methyl glucamide, lauryl methylglucamide, oleoyl methylglucamide oleate, stearoyl methylglucamide stearate, sunfloweroyl methylglucamide, and tocopheryl succinate methylglucamide.

Nonlimiting examples of alkoxylated fatty amides include PEG-20 Cocamide MEA, PEG-2 Cocamide, PEG-3 Cocamide, PEG-4 Cocamide, PEG-5 Cocamide, PEG-6 Cocamide, PEG-7 Cocamide, PEG-3 Lauramide, PEG-5 Lauramide, PEG-3 Oleamide, PEG-9 Oleamide, PEG-4 Stearamide, PEG-10 Stearamide, PPG-2 Cocamide, PPG-2 Hydroxyethyl Cocamide, PPG-2 Hydroxyethyl Coco/Isostearamide, and combinations thereof. Commercially available alkoxylated fatty amides include, but are not limited to, any of the alkoxylated fatty amides under the brand name PROTAMIDE™ (available from Protameen Chemicals, Totowa, NJ); or SERDOX@(available from Elementis Specialties, East Windsor, NJ).

The amount of the one or more fatty amides, fatty alkanolamides, and/or alkoxylated fatty amides in the hair styling compositions will vary. Nonetheless, in various embodiments, the hair styling composition includes about 1 to about 15 wt. % of the one or more fatty amides, fatty alkanolamides, and/or alkoxylated fatty amides, based on a total weight of the hair styling composition. In further embodiments, the hair styling composition includes about 1 to about 12 wt. %, about 1 to about 10 wt. %, about 1 to about 8 wt. %, about 2 to about 15 wt. %, about 2 to about 12 wt. %, about 2 to about 10 wt. %, about 2 to about 8 wt. %, about 3 to about 15 wt. %, about 3 to about 12 wt. %, about 3 to about 10 wt. %, about 3 to about 8 wt. %, about 4 to about 15 wt. %, about 4 to about 12 wt. %, about 4 to about 10 wt. %, or about 4 to about 8 wt. % of the one or more fatty amides, fatty alkanolamides, and/or alkoxylated fatty amides, based on a total weight of the hair styling composition.

(b) Non-Hydroxy Substituted Fatty Acids

Non-hydroxy substituted fatty acids include those having from about 10 to about 30 carbon atoms, from about 12 to about 24 carbon atoms, and from about 16 to about 22 carbon atoms. These fatty acids can be straight or branched chain acids and can be saturated or unsaturated. Also included herein are salts of these fatty acids. Nonlimiting examples of non-hydroxy substituted fatty acids include lauric acid, palmitic acid, stearic acid, behenic acid, arichidonic acid, oleic acid, isostearic acid, sebacic acid, and a mixture thereof. In some cases, the fatty acids are selected from the group consisting of palmitic acid, stearic acid, and a mixture thereof. In various embodiments, the non-hydroxy substituted fatty acid is selected from oleic acid, lauric acid, palmitic acid, myristic acid, stearic acid, linoleic acid, capric acid, and a combination thereof.

The amount of the one or more non-hydroxy substituted fatty acids in the hair styling composition will vary. Nonetheless, in various embodiments, the hair styling composition includes about 1 to about 12 wt. % of the one or more non-hydroxy substituted fatty acids. In further embodiments, the hair styling composition includes about 1 to about 10 wt. %, about 1 to about 8 wt. %, about 2 to about 12 wt. %, about 2 to about 10 wt. %, about 2 to about 8 wt. %, about 3 to about 12 wt. %, about 3 to about 10 wt. %, about 3 to about 8 wt. %, or about 3 to about 7 wt. % one or more non-hydroxy substituted fatty acids, based on a total weight of the hair treatment composition.

(c) Hydroxy Substituted Fatty Acids

Hydroxy substituted fatty acids include those having from about 10 to about 30 carbon atoms, from about 12 to about 24 carbon atoms, and from about 16 to about 22 carbon atoms. These fatty acids can be straight or branched chain acids and can be saturated or unsaturated. Also included herein are salts of these fatty acids. Nonlimiting examples of hydroxy substituted fatty acids include of hydroxy substituted fatty acids include 12-hydroxystearic acid, 9,10-dihydroxyoctadecanoic acid, 9,10,18-trihydroxyoctadecanoic acid, lesquerolic acid, 15-hydroxyhexadecanoic acid, isoricinoleic acid, densipolic acid, 14-hydroxy-eicosa-cis-11-cis-17-dienoic acid, 2-hydroxyoleic acid, 2-hydroxylinoleic acid, 18-hydroxystearic acid, 15-hydroxylinoleic acid, and a combination thereof.

The amount of the one or more hydroxy substituted fatty acids in the hair styling composition will vary. Nonetheless, in various embodiments, the hair styling composition include about 0.5 to about 8 wt. % of the one or more hydroxy-substituted fatty acids. In further embodiments, the hair styling composition includes about 1 to about 0.5 to about 6 wt. %, about 0.5 to about 5 wt. %, about 0.5 to about 4 wt. %, about 1 to about 8 wt. %, about 1 to about 6 wt. %, about 1 to about 5 wt. %, about 1 to about 4 wt. %, about 1.5 to about 8 wt. %, about 1.5 to about 6 wt. %, about 1.5 to about 5 wt. %, or about 1.5 to about 4 wt. % of the one or more hydroxy substituted fatty acids, based on a total weight of the hair treatment composition.

In instances where the hair styling composition includes the one or more hydroxy-substituted fatty acids of (c), the one more non-hydroxy substituted fatty acids of (b) and the one or more hydroxy-substituted fatty acids of (c) are in amounts as described throughout the disclosure. The weight ratio of (b) to (c) will vary.

Nonetheless, in various embodiments, the weight ratio of (b) to (c) is about 10:1 to about 1:1 ((b):(c)). In further embodiments, the weight ratio of (b) to (c) is about 8:1 to about 1:1, about 6:1 to about 1:1, about 5:1 to about 1:1, about 4:1 to about 1:1, about 3:1 to about 1:1, about 10:1 to >1:1, about 8:1 to >1:1, about 6:1 to >1:1, about 5:1 to >1:1, about 4:1 to >1:1, about 3:1 to >1:1, about 10:1 to about 1.5:1, about 8:1 to about 1.5:1, about 6:1 to about 1.5:1, about 5:1 to about 1.5:1, about 4:1 to about 1.5:1, about 3:1 to about 1.5:1, about 10:1 to about 2:1, about 8:1 to about 2:1, about 6:1 to about 2:1, about 5:1 to about 2:1, about 4:1 to about 2:1, or about 3:1 to about 2:1.

(d) Low-Polar Oils

The polarity of an oil is defined as the polarity index (interfacial tension) of the oil with respect to water. The polarity is determined using a ring tensiometer (e.g., Kross K 10), which measures the interfacial tension in mN/m in analogy to the ASTM method D971-99a (2004). For the purposes of the present invention, "low-polar oil" means an oil having a polarity index of 5 mN/m or higher and includes nonpolar oils.

The low-polar oils include hydrocarbon oils, silicone oils, and mixtures thereof. The low-polar oils may be nonionic lipophilic compounds that are water insoluble and liquid at room temperature (25° C.). The term "water insoluble" refers to a compound having a solubility in water of less than 1% at spontaneous pH (at atmospheric pressure and 25° C.). The low-polar hydrocarbon oils include volatile hydrocarbon oils, non-volatile hydrocarbon oils, and mixtures thereof. Suitable volatile low-polar hydrocarbon oils include linear or branched, optionally cyclic, C5-C20 lower alkanes. Examples include, but are not limited to pentane, hexane, heptane, decane, undecane, dodecane, tridecane, tetradecane, and isoparaffins, for example, isodecane, isododecane and isohexadecane.

Suitable non-volatile, low-polar hydrocarbon oils include linear or branched hydrocarbons containing at least 20 carbon atoms, such as paraffinic hydrocarbons and olefins. Examples of such hydrocarbon oils include C24-28 olefins, C30-45 olefins, C20-40 isoparaffins, hydrogenated polyisobutene, polyisobutene, polydecene, hydrogenated polydecene, mineral oil, petrolatum, pentahydrosqualene, squalene, squalane, and mixtures thereof. Suitable non-volatile silicone oils are synthetic polymeric compounds in which the silicon atoms are bonded together via oxygen atoms. The silicone oils can be non-volatile and insoluble in the aqueous phase. By non-volatile is meant that the silicone has a very low vapor pressure at ambient temperature conditions (e.g., less than 2 mm Hg at 20° C.). The non-volatile silicone oils typically have a boiling point above about 250° C., or above about 260° C., or above about 275° C.

The non-volatile silicone oils have a viscosity ranging from about above about 25 to about 1,000,000 mPa-s at 25° C., or from about 100 to about 600,000 mPa-s, or from about 1000 to about 100,000 mPa-s, or from about 2,000 to about 50,000 mPa-s, or from about 4,000 to about 40,000 mPa-s. In various embodiments, the silicone oils have an average molecular weight below about 200,000 Daltons. The average molecular weight can typically range from about 400 to about 199,000 Daltons, or from about 500 to about 150,000 Daltons, or from about 1,000 to about 100,000 Daltons, or from about 5,000 to about 65,000 Daltons. In various embodiments, the silicone oils suitable as low-polar oils are polyorganosiloxane materials selected from polyalkylsiloxanes, polyarylsiloxanes, polyalkylarylsiloxanes, and mixtures thereof. Methyl substituted polyorganosiloxanes are also known as polydimethylsiloxanes (PDMS) or dimethicone (INCI).

In various embodiments, the low-polar oil is a natural oil, in particular a vegetable oil. Nonlimiting examples of natural oils include acai, almond sweet, aloes vera, andiroba, apricot kernel, arnica, argan, avocado, babassu, boabab, black berry seed, black cumin, black currant seed, blueberry, borage, brazil nut, brocoli seed, buriti, calendula, camellia seed, canola, copaiba balsam, cape chestnut (yangu), carrot (daucus carrota), castor, chardonnay grape, chaulmoogra, cherry Kernel, chia seed, chickweed, coconut, coconut fractionated, cotton seed, comfrey, corn, crambe seed, cranberry seed, cucumber seed, echium seed, egg, evening primrose, emu, flax seed, grape seed, hazelnut, hemp seed, horsechest nut seed, jojoba, karanj seed, kiwi seed, kukuinut, macadamia nut, marula, marshmallow, manketti, meadowfoam, milk thistle seed, moringa, mullein, mustard seed, neem, olive, palm, papaya seed, passionflower seed, peach kernel, peanut, perilla, pomegranate, pumpkin seed, raspberry seed, rice bran, rosehip, St. John's Wort oil, safflower, sea buckthorn pulp, sheabutter oil, sesame roasted, sesame seed, soya been, sunflower, tamanu (*Calophyllum inophyllum*), thistle, tomato, turkey red, sangre de drago, walnut, watermelon seed, wheatgerm, and any combination thereof. In a preferred embodiment, the low-polar oils is a natural oil selected from olive oil, sunflower oil, soybean oil, peanut oil, rapeseed oil, oil of almond, palm oil, coconut oil, palm kernel oil and the like, and mixtures thereof.

In various embodiments, the hair styling composition are free or essentially of silicone oils, regardless of polarity. In fact, in various embodiments, the hair styling composition may be free or essentially free of all silicone containing materials (silicone oils, silicone-containing emulsifiers, silicone elastomers, etc.).

The amount of the one or more low-polar oils in the hair styling compositions is typical at least about 70 wt. %, based on a total weight of the hair styling composition. Nonetheless, in various embodiments, about 72 to about 95 wt. % of the one or more low-polar oils, based on a total weight of the hair styling composition. In further embodiments, the hair treatment composition includes about 72 to about 90 wt. %, about 72 to about 88 wt. %, about 72 to about 85 wt. %, about 75 to about 95 wt. %, about 75 to about 90 wt. %, about 75 to about 88 wt. %, about 75 to about 85 wt. %, about 80 to about 95 wt. %, about 80 to about 90 wt. %, or about 80 to about 85 wt. % of the one or more low-polar oils, based on a total weight of the hair styling composition.

(e) Alkoxylated Polyol Ester

The hair styling composition optionally include or exclude (or are essentially free from) one or more alkoxylated polyol esters. In a preferred embodiments, the hair styling composition include one or more alkoxylated polyol esters. Nonlimiting examples of alkoxylated polyol esters include pegylated derivatives of propylene glycol oleate, propylene glycol caprylate/caprate, propylene glycol cocoate, propylene glycol stearate, and a mixture thereof. In some embodiments, the alkoxylated polyol esters may be chosen from PEG-55 propylene glycol oleate, PEG-6 propylene glycol caprylate/caprate, PEG-8 propylene glycol cocoate, PEG-25 propylene glycol stearate, and PEG-120 propylene glycol stearate, and a mixture thereof. In a preferred embodiment, the one or more alkoxylated polyol esters are selected from PEG-55 propylene glycol oleate, PEG-6 propylene glycol caprylate/caprate, PEG-8 propylene glycol cocoate, PEG-25 propylene glycol stearate, and PEG-120 propylene glycol stearate, and a mixture thereof. A particularly useful alkoxylated polyol esters is PEG-55 propylene glycol oleate.

The amount of the one or more alkoxylated polyol esters in the hair styling composition, if present, will vary. Nonetheless, in various embodiments, the hair styling composition includes about 0.1 to about 10 wt. % of the one or more alkoxylated polyol esters, based on a total weight of the hair styling composition. In further embodiments, the hair styling composition includes about 0.1 to about 8 wt. %, about 0.1 to about 6 wt. %, about 0.1 to about 5 wt. %, about 0.5 to about 10 wt. %, about 0.5 to about 8 wt. %, about 0.5 to about 6 wt. %, about 0.5 to about 5 wt. %, about 1 to about 10 wt. %, about 1 to about 8 wt. %, about 1 to about 6 wt. %, about 1 to about 5 wt. %, or about 1 to about 4 wt. % of the one or more alkoxylated polyol esters, based on a total weight of the hair styling composition.

(f) Water Soluble Organic Solvent

The hair styling composition optionally include or exclude (or are essentially free from) one or more water soluble organic solvents. In a preferred embodiment, the hair styling composition includes one or more water soluble organic solvents.

The term "water soluble organic solvent" is interchangeable with the terms "water soluble solvent" and "water-miscible solvent" and means a compound that is liquid at 25° C. and at atmospheric pressure (760 mmHg), and it has a solubility of at least 50% in water under these conditions. In some cases, the water-soluble solvents has a solubility of at least 60%, 70%, 80%, or 90%. Non-limiting examples of water-soluble solvents include, for example, organic solvents selected from glycerin, alcohols (for example, C1-12, C1-10, C1-8, or C1-4 alcohols), polyols (polyhydric alcohols), glycols, and a mixture thereof.

Non-limiting examples of water soluble organic solvents include monoalcohols and polyols such as ethyl alcohol, isopropyl alcohol, propyl alcohol, benzyl alcohol, and phenylethyl alcohol, or glycols or glycol ethers such as, for example, monomethyl, monoethyl and monobutyl ethers of ethylene glycol, propylene glycol or ethers thereof such as, for example, monomethyl ether of propylene glycol, butylene glycol, hexylene glycol, dipropylene glycol as well as alkyl ethers of diethylene glycol, for example monoethyl ether or monobutyl ether of diethylene glycol. Other suitable examples of organic solvents are ethylene glycol, propylene glycol, butylene glycol, hexylene glycol, propane diol, and glycerin. The organic solvents can be volatile or non-volatile compounds.

Further non-limiting examples of water soluble organic solvents include alkanediols (polyhydric alcohols) such as glycerin, 1,2,6-hexanetriol, trimethylolpropane, ethylene glycol, propylene glycol, diethylene glycol, triethylene glycol, tetraethylene glycol, pentaethylene glycol, dipropylene glycol, 2-butene-1,4-diol, 2-ethyl-1,3-hexanediol, 2-methyl-2,4-pentanediol, (caprylyl glycol), 1,2-hexanediol, 1,2-pentanediol, and 4-methyl-1,2-pentanediol; alkyl alcohols having 1 to 4 carbon atoms such as ethanol, methanol, butanol, propanol, and isopropanol; glycol ethers such as ethylene glycol monomethyl ether, ethylene glycol monoethyl ether, ethylene glycol monobutyl ether, ethylene glycol monomethyl ether acetate, diethylene glycol monomethyl ether, diethylene glycol monoethyl ether, diethylene glycol mono-n-propyl ether, ethylene glycol mono-iso-propyl ether, diethylene glycol mono-iso-propyl ether, ethylene glycol mono-n-butyl ether, ethylene glycol mono-t-butyl ether, diethylene glycol mono-t-butyl ether, 1-methyl-1-methoxybutanol, propylene glycol monomethyl ether, propylene glycol monoethyl ether, propylene glycol mono-t-butyl ether, propylene glycol mono-n-propyl ether, propylene glycol mono-iso-propyl ether, dipropylene glycol monomethyl ether, dipropylene glycol monoethyl ether, dipropylene glycol mono-n-propyl ether, and dipropylene glycol mono-iso-propyl ether; 2-pyrrolidone, N-methyl-2-pyrrolidone, 1,3-dimethyl-2-imidazolidinone, formamide, acetamide, dimethyl sulfoxide, sorbit, sorbitan, acetine, diacetine, triacetine, sulfolane, and a mixture thereof.

Polyhydric alcohols are useful. Examples of polyhydric alcohols include glycerin, ethylene glycol, diethylene glycol, triethylene glycol, propylene glycol, dipropylene glycol, tripropylene glycol, 1,3-butanediol, 2,3-butanediol, 1,4-butanediol, 3-methyl-1,3-butanediol, 1,5-pentanediol, tetraethylene glycol, 1,6-hexanediol, 2-methyl-2,4-pentanediol, polyethylene glycol, 1,2,4-butanetriol, 1,2,6-hexanetriol, and a mixture thereof. Polyol compounds may also be used. Non-limiting examples include the aliphatic diols, such as 2-ethyl-2-methyl-1,3-propanediol, 3,3-dimethyl-1,2-butanediol, 2,2-diethyl-1,3-propanediol, 2-methyl-2-propyl-1,3-propanediol, 2,4-dimethyl-2,4-pentanediol, 2,5-dimethyl-2,5-hexanediol, 5-hexene-1,2-diol, and 2-ethyl-1,3-hexanediol, and a mixture thereof.

The amount of the one or more water soluble organic solvents in the hair treatment composition, if present, will vary. Nonetheless, in various embodiments, the hair styling composition includes about 0.1 to about 10 wt. % of the one or more water soluble organic solvents, based on a total weight of the hair styling composition. In further embodiments, the hair styling composition includes about 0.1 to about 8 wt. %, about 0.1 to about 6 wt. %, about 0.1 to about 5 wt. %, about 0.5 to about 10 wt. %, about 0.5 to about 8 wt. %, about 0.5 to about 6 wt. %, about 0.5 to about 5 wt. %, about 1 to about 10 wt. %, about 1 to about 8 wt. %, about 1 to about 6 wt. %, or about 1 to about 5 wt. % of the one or more water soluble organic solvents, based on a total weight of the hair styling composition.

(g) Film-Forming Polymers

The hair styling composition may optionally include or exclude (or be essentially free from) one or more film-forming polymers, for example, one or more nonionic film forming polymers, one or more amphoteric hair film forming polymers, or a combination thereof. In various embodiments, the hair styling composition is free or essentially free from film-forming polymers.

Non-limiting examples of nonionic film-forming polymers include vinylpyrrolidone homopolymers; copolymers of vinylpyrrolidone and of vinyl acetate; polyalkyloxazolines; vinyl acetate homopolymers; copolymers of vinyl acetate and of acrylic ester; copolymers of vinyl acetate and of ethylene; copolymers of vinyl acetate and of maleic ester; copolymers of polyethylene and of maleic anhydride; alkyl acrylate homopolymers and alkyl methacrylate homopolymers; acrylic ester copolymers; copolymers of acrylonitrile and of a non-ionic monomer; and a mixture thereof. In some cases, particularly useful nonionic film-forming polymers include vinylpyrrolidone homopolymers and copolymers of vinylpyrrolidone and of vinyl acetate, for example, polyvinylpyrrolidone/vinyl acetate (VP/VA) copolymer. In some instances, nonionic film forming polymers of the present disclosure are selected from the group consisting of vinylpyrrolidone homopolymers, copolymers of vinylpyrrolidone and of vinyl acetate, and a mixture thereof. Vinylpyrrolidone homopolymers (INCI name: polyvinylpyrrolidone) are commercially available from Ashland Specialty Ingredients under the tradename PVP K. Copolymers of vinylpyrrolidone and of vinyl acetate (INCI name: VP/VA copolymer) are commercially available from BASF under the tradename Luviskol VA.

Nonlimiting examples of amphoteric film-forming polymers include:
(1) polymers resulting from the copolymerization of a monomer derived from a vinyl compound bearing a carboxylic group such as, more particularly, acrylic acid, methacrylic acid, maleic acid, α-chloroacrylic acid, and a basic monomer derived from a substituted vinyl compound containing at least one basic atom, such as, more particularly, dialkylaminoalkyl methacrylates and acrylates, dialkylaminoalkylmethacrylamides and -acrylamides;
(2) polymers containing units derived from:
 a) at least one monomer chosen from acrylamides and methacrylamides substituted on the nitrogen with an alkyl radical,
 b) at least one acidic comonomer containing one or more reactive carboxylic groups, and
 c) at least one basic comonomer such as esters containing primary, secondary, tertiary and quaternary amine substituents of acrylic and methacrylic acids and the product of quaternization of dimethylaminoethyl methacrylate with dimethyl or diethyl sulphate.

The N-substituted acrylamides or methacrylamides which may be useful are groups in which the alkyl radicals contain from 2 to 12 carbon atoms and more particularly N-ethylacrylamide, N-tert-butylacrylamide, N-tert-octylacrylamide, N-octylacrylamide, N-decylacrylamide, N-dodecylacrylamide and the corresponding methacrylamides.

The acidic comonomers include acrylic acid, methacrylic acid, crotonic acid, itaconic acid, maleic acid and fumaric acid and alkyl monoesters, having 1 to 4 carbon atoms, of maleic or fumaric acids or anhydrides.

In some cases, preferred basic comonomers are aminoethyl, butylaminoethyl, N,N'-dimethylaminoethyl and N-tert-butylaminoethyl methacrylates. Octylacrylamide/acrylates/butylaminoethyl methacrylate copolymer such as the products sold under the name Amphomer or Balance 47 (formerly Lovocryl 47) by the company Akzo Nobel can be used.

(3) crosslinked and alkylated polyamino amides partially or totally derived polyamino amides.
(4) polymers containing zwitterionic units of formula:

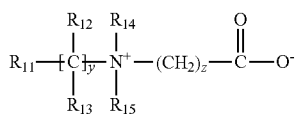

in which $R_{11}$ denotes a polymerizable unsaturated group, such as an acrylate, methacrylate, acrylamide or methacrylamide group, y and z represent an integer from 1 to 3, $R_{12}$ and $R_{13}$ represent a hydrogen atom or methyl, ethyl or propyl, and $R_{14}$ and $R_{15}$ represent a hydrogen atom or an alkyl radical such that the sum of the carbon atoms in $R_{14}$ and $R_{15}$ does not exceed 10.

The polymers comprising such units can also contain units derived from non-zwitterionic monomers such as dimethyl or diethylaminoethyl acrylate or methacrylate or alkyl acrylates or methacrylates, acrylamides or methacrylamides or vinyl acetate: By way of example, mention may be made of the copolymer of methyl methacrylate/dimethyl carboxymethylammonio methyl ethylmethacrylate.

(5) Polymers derived from chitosan.
(6) Polymers derived from the N-carboxyalkylation of chitosan, such as N-carboxymethylchitosan or N-carboxybutylchitosan sold under the name "Evalsan" by the company Jan Dekker.
(7) Polymers corresponding to the general formula:

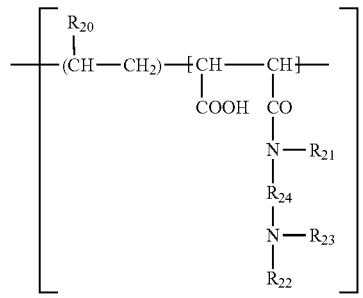

in which $R_{20}$ represents a hydrogen atom, a $CH_3O$, $CH_3CH_2O$ or phenyl radical, $R_{21}$ denotes hydrogen or a lower alkyl radical such as methyl or ethyl, $R_{22}$ denotes hydrogen or a lower alkyl radical such as methyl or ethyl, $R_{23}$ denotes a lower alkyl radical such as methyl or ethyl or a radical corresponding to the formula: -R.sub.24-N($R_{22}$).sub.2, $R_{24}$ representing a —$CH_2$—$CH_2$, —$CH_2$—$CH_2$—$CH_2$— or —$CH_2$—CH($CH_3$)-group, $R_{22}$ having the meanings mentioned above, as well as the higher homologues of these radicals and containing up to 6 carbon atoms.

(8) Amphoteric polymers of the type -D-X-D-X chosen from:
  a) polymers obtained by the action of chloroacetic acid or sodium chloroacetate on compounds containing at least one unit of formula:

-D-X-D-X-D-    (I)

where D denotes a radical

and X denotes the symbol E or E', E or E', which may be identical or different, denotes a divalent radical which is an alkylene radical containing a straight or branched chain containing up to 7 carbon atoms in the main chain, which is unsubstituted or substituted with hydroxyl groups and which can contain, in addition to the oxygen, nitrogen and sulphur atoms, 1 to 3 aromatic and/or heterocyclic rings; the oxygen, nitrogen and sulphur atoms being present in the form of ether, thioether, sulphoxide, sulphone, sulphonium, alkylamine or alkenylamine groups, hydroxyl, benzylamine, amine oxide, quaternary ammonium, amide, imide, alcohol, ester and/or urethane groups.
  b) Polymers of formula:

-D-X-D-X-    (I')

in which D denotes a radical

and X denotes the symbol E or E' and at least once E'; E having the meaning given above and E' is a divalent radical which is an alkylene radical with a straight or branched chain having up to 7 carbon atoms in the main chain, which is unsubstituted or substituted with one or more hydroxyl radicals and containing one or more nitrogen atoms, the nitrogen atom being substituted with an alkyl chain which is optionally interrupted by an oxygen atom and necessarily containing one or more carboxyl functions or one or more hydroxyl functions and betainized by reaction with chloroacetic acid or sodium chloroacetate.

(9) (C1-C5)alkyl vinyl ether/maleic anhydride copolymers, the maleic anhydride being partially modified by semiamidation with an N,N-dialkylaminoalkylamine such as N,N-dimethyl-aminopropylamine or by semiesterification with an N,N-dialkanolamine. These copolymers can also contain other vinyl comonomers such as vinylcaprolactam.

The amphoteric film-forming polymers which that may be particularly useful are those of family (3), such as the copolymers whose CTFA name is octylacrylamide/acrylates/butylaminoethyl methacrylate copolymer, such as the products sold under the names Amphomer LV 71 by the company Akzo Nobel.

In some instances, the one or more amphoteric film-forming polymers are selected from the group consisting of:
  (i) polymers resulting from the copolymerization of a monomer derived from a vinyl compound bearing a carboxylic group selected from the group consisting of acrylic acid, methacrylic acid, maleic acid, and α-chloroacrylic acid, and a basic monomer derived from a substituted vinyl compound containing at least one basic atom;
  (ii) polymers containing units derived from:
    a) at least one monomer selected from the group consisting of acrylamides and methacrylamides substituted on the nitrogen with an alkyl radical,
    b) at least one acidic comonomer containing one or more reactive carboxylic groups, and
    c) at least one basic comonomer ester containing primary, secondary, tertiary or quaternary amine substituents of acrylic and methacrylic acids or the product of quaternization of dimethylaminoethyl methacrylate with dimethyl or diethyl sulphate;
  (iii) crosslinked and alkylated polyamino amides partially or totally derived polyamino amides; and
  (vi) copolymers of methyl methacrylate/dimethyl carboxymethyl-ammoniomethylethylmethacrylate.

The amount of the one or more film-forming polymers, if present, will vary. Nonetheless, in various embodiments, the hair styling composition includes about 0.01 to about 10 wt. % of the one or more film-forming polymers, preferably one or more nonionic film-forming polymers, based on a total weight of the hair styling composition. In further embodiments, the hair styling composition includes about 0.01 to about 8 wt. %, about 0.01 to about 6 wt. %, about 0.01 to about 5 wt. %, about 0.01 to about 3 wt. %, about 0.05 to about 10 wt. %, about 0.05 to about 8 wt. %, about 0.05 to about 6 wt. %, about 0.05 to about 5 wt. %, about 0.05 to about 3 wt. %, about 0.1 to about 10 wt. %, about 0.1 to about 8 wt. %, about 0.1 to about 6 wt. %, about 0.1 to about 5 wt. %, about 0.1 to about 3 wt. % of the one or more film-forming polymers, preferably nonionic film forming polymers, based on a total weight of the hair styling composition.

(h) Cationic Conditioning Polymers

The hair styling composition may optionally include or exclude (or be essentially free from) one or more cationic conditioning polymers. In various embodiments, the hair styling composition is free or essentially free from cationic conditioning polymers.

Non-limiting examples of cationic polymers include copolymers of 1-vinyl-2-pyrrolidine and 1-vinyl-3-methylimidazolium salt (e.g., chloride salt) (referred to as Polyquaternium-16); copolymers of 1-vinyl-2-pyrrolidine and dimethylaminoethyl methacrylate (referred to as Polyquaternium-11); cationic diallyl quaternary ammonium-containing polymer including, for example, dimethyldiallyammonium chloride homopolymer and copolymers of acrylamide and dimethyldiallyammonium chloride (referred to as Polyquaternium-6 and Polyquaternium-7); polysaccharide polymers, such as cationic cellulose derivatives and cationic starch derivatives. Cationic cellulose is available as salts of hydroxyethyl cellulose reacted with trimethyl ammonium substituted epoxide (referred to as Polyquaternium-10).

Another type of cationic cellulose includes the polymeric quaternary ammonium salts of hydroxyethyl cellulose reacted with lauryl dimethyl ammonium-substituted epoxide (referred to as Polyquaternium-24). Additionally, or alternatively, the cationic conditioning polymers may include or be chosen from cationic guar gum derivatives, such as guar hydroxypropyltrimonium chloride.

In certain embodiments, the one or more cationic conditioning polymers include cationic polysaccharide polymers, such as cationic cellulose, cationic starch, and cationic guar gum. In the context of the instant disclosure cationic polysaccharide polymers include cationic polysaccharides and polysaccharide derivatives (e.g., derivatized to be cationic), for example, resulting in cationic cellulose (cellulose derivatized to be cationic), cationic starch (derivatized to be cationic), cationic guar (guar derivatized to be cationic).

Non-limiting examples of cationic celluloses include hydroxyethylcellulose (also known as HEC), hydroxymethylcellulose, methylhydroxyethylcellulose, hydroxypropylcellulose (also known as HPC), hydroxybutylcellulose, hydroxyethylmethylcellulose (also known as methyl hydroxyethylcellulose) and hydroxypropylmethylcellulose (also known as HPMC), cetyl hydroxyethylcellulose, polyquaternium-10, polyquaternium-24, and mixtures thereof, preferably polyquaternium-10, polyquaternium-24, and mixtures thereof.

Non-limiting examples of cationic guar include guar hydroxypropyltrimonium chloride, hydroxypropyl guar hydroxypropyltrimonium chloride, Non-limiting examples of cationic starch include starch hydroxypropyltrimonium chloride, hydroxypropyl oxidized starch PG trimonium chloride, and a mixture thereof.

In various embodiments, the one or more cationic conditioning polymers are chosen from polyquaterniums. Non-limiting examples include Polyquaternium-1 (ethanol, 2,2', 2"-nitrilotris-, polymer with 1,4-dichloro-2-butene and N,N,N',N'-tetramethyl-2-butene-1,4-diamine), Polyquaternium-2, (poly[bis(2-chloroethyl) ether-alt-1,3-bis[3-(dimethylamino)propyl]urea]), Polyquaternium-4, (hydroxyethyl cellulose dimethyl diallylammonium chloride copolymer; Diallyldimethylammonium chloride-hydroxyethyl cellulose copolymer), Polyquaternium-5 (copolymer of acrylamide and quaternized dimethylammoniumethyl methacrylate), Polyquaternium-6 (poly(diallyldimethylammonium chloride)), Polyquaternium-7 (copolymer of acrylamide and diallyldimethylammonium chloride), Polyquaternium-8 (copolymer of methyl and stearyl dimethylaminoethyl ester of methacrylic acid, quaternized with dimethylsulphate), Polyquaternium-9 (homopolymer of N,N-(dimethylamino)ethyl ester of methacrylic acid, quaternized with bromomethane), Polyquaternium-10 (quaternized hydroxyethyl cellulose), Polyquaternium-11 (copolymer of vinylpyrrolidone and quaternized dimethylaminoethyl methacrylate), Polyquaternium-12 (ethyl methacrylate/abietyl methacrylate/diethylaminoethyl methacrylate copolymer quaternized with dimethyl sulfate), Polyquaternium-13 (ethyl methacrylate/oleyl methacrylate/diethylaminoethyl methacrylate copolymer quaternized with dimethyl sulfate), Polyquaternium-14 (trimethylaminoethylmethacrylate homopolymer), Polyquaternium-15 (acrylamide-dimethylaminoethyl methacrylate methyl chloride copolymer), Polyquaternium-16 (copolymer of vinylpyrrolidone and quaternized vinylimidazole), Polyquaternium-17 (adipic acid, dimethylaminopropylamine and dichloroethylether copolymer), Polyquaternium-18 (azelanic acid, dimethylaminopropylamine and dichloroethylether copolymer), Polyquaternium-19 (copolymer of polyvinyl alcohol and 2,3-epoxypropylamine), Polyquaternium-20 (copolymer of polyvinyl octadecyl ether and 2,3-epoxypropylamine), Polyquaternium-22 (copolymer of acrylic acid and diallyldimethylammonium chloride), Polyquaternium-24 (quaternary ammonium salt of hydroxyethyl cellulose reacted with a lauryl dimethyl ammonium substituted epoxide), Polyquaternium-27 (block copolymer of Polyquaternium-2 and Polyquaternium-17), Polyquaternium-28 (copolymer of vinylpyrrolidone and methacrylamidopropyl trimethylammonium), Polyquaternium-29 (chitosan modified with propylen oxide and quaternized with epichlorhydrin), Polyquaternium-30 (ethanaminium, N-(carboxymethyl)-N,N-dimethyl-2-[(2-methyl-1-oxo-2-propen-1-yl)oxy]-, inner salt, polymer with methyl 2-methyl-2-propenoate), Polyquaternium-31 (N,N-dimethylaminopropyl-N-acrylamidine quaternized with diethylsulfate bound to a block of polyacrylonitrile), Polyquaternium-32 (poly(acrylamide 2-methacryloxyethyltrimethyl ammonium chloride)), Polyquaternium-33 (copolymer of trimethylaminoethylacrylate salt and acrylamide), Polyquaternium-34 (copolymer of 1,3-dibromopropane and N,N-diethyl-N',N'-dimethyl-1,3-propanediamine), Polyquaternium-35 (methosulphate of the copolymer of methacryloyloxyethyltrimethylammonium and of methacryloyloxyethyldimethylacetylammonium), Polyquaternium-36 (copolymer of N,N-dimethylaminoethylmethacrylate and buthylmethacrylate, quaternized with dimethylsulphate), Polyquaternium-37 (poly(2-methacryloxyethyltrimethylammonium chloride)), Polyquaternium-39 (terpolymer of acrylic acid, acrylamide and diallyldimethylammonium Chloride), Polyquaternium-42 (poly[oxyethylene(dimethylimino)ethylene (dimethylimino)ethylene dichloride]), Polyquaternium-43 (copolymer of acrylamide, acrylamidopropyltrimonium chloride, 2-amidopropylacrylamide sulfonate and dimethylaminopropylamine), Polyquaternium-44 (3-Methyl-1-vinylimidazolium methyl sulfate-N-vinylpyrrolidone copolymer), Polyquaternium-45 (copolymer of (N-methyl-N-ethoxyglycine)methacrylate and N,N-dimethylaminoethylmethacrylate, quaternized with dimethyl sulphate), Polyquaternium-46 (terpolymer of vinylcaprolactam, vinylpyrrolidone, and quaternized vinylimidazole), Polyquaternium-47 (terpolymer of acrylic acid, methacrylamidopropyl trimethylammonium chloride, and methyl acrylate), and/or Polyquaternium-67.

In various embodiments, the one or more cationic conditioning polymers are chosen from cationic cellulose derivatives, quaternized hydroxyethyl cellulose (e.g., polyquaternium-10), cationic starch derivatives, cationic guar gum derivatives, copolymers of acrylamide and dimethyldiallyammonium chloride (e.g., polyquaternium-7), polyquaterniums, and a mixture thereof. For example, the cationic polymer(s) may be selected from polyquaterniums, for example, polyquaterniums selected from polyquaternium-4, polyquaternium-5, polyquaternium-6, polyquaternium-7, polyquaternium-10, polyquaternium-22, polyquaternium-37, polyquaternium-39, polyquaternium-47, polyquaternium-53, polyquaternium-67 and a mixture thereof. A combination of two or more polyquaterniums can be useful. A particularly preferred and useful cationic polymer is polyquaternium-10.

The cationic polymers may be a polyquaternium. In certain embodiments, the cationic surfactants may be polyquaterniums selected from polyquaternium-1, polyquaternium-2, polyquaternium-3, polyquaternium-4, polyquaternium-5, polyquaternium-6, polyquaternium-7, polyquaternium-8, polyquaternium-9, polyquaternium-10, polyquaternium-11, polyquaternium-12, polyquaternium- 13, polyquaternium-14, polyquaternium-15, polyquaternium-16, polyquaternium-17, polyquaternium-18, polyquaternium-19, polyquaternium-20, polyquaternium-21, polyquaternium-22, polyquaternium-23, polyquaternium-24, polyquaternium-25, polyquaternium-26, polyquaternium-27, polyquaternium-28, polyquaternium-29, polyquaternium-30, polyquaternium-40, polyquaternium-41, polyquaternium-42, polyquaternium-43, polyquaternium-44, polyquaternium-45, polyquaternium-46, polyquaternium-47, polyquaternium-48, polyquaternium-49, polyquaternium-50, polyquaternium-51, polyquaternium-52, polyquaternium-53, polyquaternium-54, polyquaternium-55, polyquaternium-56, polyquaternium-57, polyquaternium-58, polyquaternium-59, polyquaternium-60, polyquaternium-61, polyquaternium-62, polyquaternium-63, polyquaternium-64, polyquaternium-65, polyquaternium-66, polyquaternium-67, etc. In some cases, preferred polyquaternium compounds include polyquaternium-10, polyquaternium-11, polyquaternium-67, and a mixture thereof.

In some embodiments, the one or more cationic conditioning polymers are chosen from cationic proteins and cationic protein hydrolysates (e.g., hydroxypropyltrimonium hydrolyzed wheat protein), quaternary diammonium polymers (e.g., hexadimethrine chloride), copolymers of acrylamide and dimethyldiallyammonium chloride, and mixtures thereof.

The cationic conditioning polymers may be homopolymers or formed from two or more types of monomers. The molecular weight of the polymer may be between 5,000 and 10,000,000, typically at least 10,000, and preferably in the range 100,000 to about 2,000,000. These polymers will typically have cationic nitrogen containing groups such as quaternary ammonium or protonated amino groups, or a mixture thereof.

The cationic charge density is suitably at least 0.1 meq/g, preferably above 0.8 or higher. In some instances, the cationic charge density does not exceed 3 meq/g, or does not exceed 2 meq/g. The charge density can be measured using the Kjeldahl method and can be within the above limits at the desired pH of use, which will in general be from about 3 to 9 and preferably between 4 and 8.

The cationic nitrogen-containing group will generally be present as a substituent on a fraction of the total monomer units of the cationic conditioning polymer. Thus when the polymer is not a homopolymer it can contain spacer non-cationic monomer units.

Suitable cationic conditioning polymers include, for example, copolymers of vinyl monomers having cationic amine or quaternary ammonium functionalities with water soluble spacer monomers such as (meth)acrylamide, alkyl and dialkyl (meth)acrylamides, alkyl (meth)acrylate, vinyl caprolactone and vinyl pyrrolidine. The alkyl and dialkyl substituted monomers preferably have C1-C7 alkyl groups, more preferably C1-C3 alkyl groups. Other suitable spacers include vinyl esters, vinyl alcohol, maleic anhydride, propylene glycol and ethylene glycol.

The cationic amines can be primary, secondary or tertiary amines, depending upon the particular species and the pH of the composition.

Amine substituted vinyl monomers and amines can be polymerized in the amine form and then converted to ammonium by quaternization.

Suitable cationic amino and quaternary ammonium monomers include, for example, vinyl compounds substituted with dialkyl amincalkyl acrylate, dialkylamino alkylmethacrylate, monoalkylaminoalkyl acrylate, monoalkylaminoalkyl methacrylate, trialkyl methacryloxyalkyl ammonium salt, trialkyl acryloxyalkyl ammonium salt, diallyl quaternary ammonium salts, and vinyl quaternary ammonium monomers having cyclic cationic nitrogen-containing rings such as pyridinium, imidazolium, and quaternized pyrrolidine, e.g., alkyl vinyl imidazolium, and quaternized pyrrolidine, e.g., alkyl vinyl imidazolium, alkyl vinyl pyridinium, alkyl vinyl pyrrolidine salts. The alkyl portions of these monomers are preferably lower alkyls such as the $C_1$-$C_3$ alkyls, more preferably $C_1$ and $C_2$ alkyls.

Suitable amine-substituted vinyl monomers include dialkylaminoalkyl acrylate, dialkylaminoalkyl methacrylate, dialkylaminoalkyl acrylamide, and dialkylaminoalkyl methacrylamide, wherein the alkyl groups are preferably $C_1$-$C_7$ hydrocarbyls, more preferably $C_1$-$C_3$, alkyls.

The cationic conditioning polymers can comprise mixtures of monomer units derived from amine- and/or quaternary ammonium-substituted monomer and/or compatible spacer monomers.

Suitable cationic conditioning polymers include, for example: copolymers of 1-vinyl-2-pyrrolidine and 1-vinyl-3-methyl-imidazolium salt (e.g., Chloride salt) (referred to as Polyquaternium-16) such as those commercially available from BASF under the LUVIQUAT tradename (e.g., LUVIQUAT FC 370); copolymers of 1-vinyl-2-pyrrolidine and dimethylaminoethyl methacrylate (referred to as Polyquaternium-11) such as those commercially from Gar Corporation (Wayne, N.J., USA) under the GAFQUAT tradename (e.g., GAFQUAT 755N); and cationic diallyl quaternary ammonium-containing polymer including, for example, dimethyldiallyammonium chloride homopolymer and copolymers of acrylamide and dimethyldiallyammonium chloride (referred to as Polyquaternium-6 and Polyquaternium-7).

Other cationic conditioning polymers that can be used include polysaccharide polymers, such as cationic cellulose derivatives and cationic starch derivatives. Cationic cellulose is available from Amerchol Corp. (Edison, N.J., USA) in their Polymer JR (trade mark) and LR (trade mark) series of polymers, as salts of hydroxyethyl cellulose reacted with trimethyl ammonium substituted epoxide (referred to as Polyquaternium-10). Another type of cationic cellulose includes the polymeric quaternary ammonium salts of hydroxyethyl cellulose reacted with lauryl dimethyl ammonium-substituted epoxide (referred to as Polyquaternium-24). These materials are available from Amerchol Corp. (Edison, N.J., USA) under the tradename Polymer LM-200.

Other cationic conditioning polymers that can be used include cationic guar gum derivatives, such as guar hydroxypropyltrimonium chloride.

Polyquaterniums include Polyquaternium-1 (ethanol, 2,2', 2'-nitrilotris-, polymer with 1,4-dichloro-2-butene and N,N,N',N'-tetramethyl-2-butene-1,4-diamine), Polyquaternium-2, (poly[bis(2-chloroethyl) ether-alt-1,3-bis[3-(dimethylamino)propyl]urea]), Polyquaternium-4, (hydroxyethyl cellulose dimethyl diallylammonium chloride copolymer; Diallyldimethylammonium chloride-hydroxyethyl cellulose copolymer), Polyquaternium-5 (copolymer of acrylamide and quaternized dimethylammoniumethyl methacrylate), polyquaternium-6 (poly(diallyldimethylammonium chloride)), Polyquaternium-7 (copolymer of acrylamide and diallyldimethylammonium chloride), Polyquaternium-8 (copolymer of methyl and stearyl dimethylaminoethyl ester of methacrylic acid, quaternized with dimethylsulphate), Polyquaternium-9 (homopolymer of N,N-(dimethylamino)ethyl ester of methacrylic acid, quaternized with bromomethane), Polyquaternium-10 (quaternized hydroxyethyl cellulose), polyquaternium-11 (copolymer of vinylpyrrolidone and quaternized dimethylaminoethyl methacrylate), Polyquaternium-12 (ethyl methacrylate/abietyl methacrylate/diethylaminoethyl methacrylate copolymer quaternized with dimethyl sulfate), Polyquaternium-13 (ethyl methacrylate/oleyl methacrylate/diethylaminoethyl methacrylate copolymer quaternized with dimethyl sulfate), Polyquaternium-14 (trimethylaminoethylmethacrylate homopolymer), Polyquaternium-15 (acrylamide-dimethylaminoethyl methacrylate methyl chloride copolymer), Polyquaternium-16 (copolymer of vinylpyrrolidone and quaternized vinylimidazole), Polyquaternium-17 (adipic acid, dimethylaminopropylamine and dichloroethylether copolymer), Polyquaternium-18 (azelanic acid, dimethylaminopropylamine and dichloroethylether copolymer), Polyquaternium-19 (copolymer of polyvinyl alcohol and 2,3-epoxypropylamine), Polyquaternium-20 (copolymer of polyvinyl octadecyl ether and 2,3-epoxypropylamine), Polyquaternium-22 (copolymer of acrylic acid and diallyldimethylammonium chloride), Polyquaternium-24 (quaternary ammonium salt of hydroxyethyl cellulose reacted with a lauryl dimethyl ammonium substituted epoxide), Polyquaternium-27 (block copolymer of Polyquaternium-2 and Polyquaternium-17), Polyquaternium-28 (copolymer of vinylpyrrolidone and methacrylamidopropyl trimethylammonium), Polyquaternium-29 (chitosan modified with propylen oxide and quaternized with epichlorhydrin), Polyquaternium-30 (ethanaminium, N-(carboxymethyl)-N,N-dimethyl-2-[(2-methyl-1-oxo-2-propen-1-yl)oxy]-, inner salt, polymer with methyl 2-methyl-2-propenoate), Polyquaternium-31 (N,N-dimethylaminopropyl-N-acrylamidine quaternized with diethylsulfate bound to a block of polyacrylonitrile), Polyquaternium-32 (poly(acrylamide 2-methacryloxyethyltrimethyl ammonium chloride)), Polyquaternium-33 (copolymer of trimethylaminoethylacrylate salt and acrylamide), Polyquaternium-34 (copolymer of 1,3-dibromopropane and N,N-diethyl-N',N'-dimethyl-1,3-propanediamine), Polyquaternium-35 (methosulphate of the copolymer of methacryloyloxyethyltrimethylammonium and of methacryloyloxyethyldimethylacetylammonium), Polyquaternium-36 (copolymer of N,N-dimethylaminoethylmethacrylate and buthylmethacrylate, quaternized with dimethylsulphate), Polyquaternium-37 (poly(2-methacryloxyethyltrimethylammonium chloride)), Polyquaternium-39 (terpolymer of acrylic acid, acrylamide and diallyldimethylammonium Chloride), Polyquaternium-42 (poly[oxyethylene(dimethylimino)ethylene (dimethylimino)ethylene dichloride]), Polyquaternium-43 (copolymer of acrylamide, acrylamidopropyltrimonium chloride, 2-amidopropylacrylamide sulfonate and dimethylaminopropylamine), Polyquaternium-44 (3-Methyl-1-vinylimidazolium methyl sulfate-N-vinylpyrrolidone copolymer), Polyquaternium-45 (copolymer of (N-methyl-N-ethoxyglycine)methacrylate and N,N-dimethylaminoethylmethacrylate, quaternized with dimethyl sulphate), Polyquaternium-46 (terpolymer of vinylcaprolactam, vinylpyrrolidone, and quaternized vinylimidazole), and Polyquaternium-47 (terpolymer of acrylic acid, methacrylamidopropyl trimethylammonium chloride, and methyl acrylate).

The amount of the one or more cationic conditioning polymers, if present, will vary. Nonetheless, in various embodiments, the hair styling composition includes about 0.01 to about 10 wt. % of the one or more cationic conditioning polymers, based on a total weight of the hair styling composition. In further embodiments, the hair styling composition includes about 0.01 to about 8 wt. %, about 0.01 to about 6 wt. %, about 0.01 to about 5 wt. %, about 0.01 to about 3 wt. %, about 0.05 to about 10 wt. %, about 0.05 to about 8 wt. %, about 0.05 to about 6 wt. %, about 0.05 to about 5 wt. %, about 0.05 to about 3 wt. %, about 0.1 to about 10 wt. %, about 0.1 to about 8 wt. %, about 0.1 to about 6 wt. %, about 0.1 to about 5 wt. %, about 0.1 to about 3 wt. % of the one or more cationic conditioning polymers, based on a total weight of the hair styling composition.

(i) Nonionic Surfactants

The hair styling composition may optionally include or exclude (or be essentially free from) one or more nonionic surfactants. Non-limiting examples of nonionic surfactants include the following:

(1) polyethylene oxide condensates of alkyl phenols, e.g., the condensation products of alkyl phenols having an alkyl group containing from about 6 to about 20 carbon atoms in either a straight chain or branched chain configuration, with ethylene oxide, the said ethylene oxide being present in amounts equal to from about 10 to about 60 moles of ethylene oxide per mole of alkyl phenol;

(2) those derived from the condensation of ethylene oxide with the product resulting from the reaction of propylene oxide and ethylene diamine products; (3) condensation products of aliphatic alcohols having from about 8 to about 18 carbon atoms, in either straight chain or branched chain configurations, with ethylene oxide, e.g., a coconut alcohol ethylene oxide condensate having from about 10 to about 30 moles of ethylene oxide per mole of coconut alcohol, the coconut alcohol fraction having from about 10 to about 14 carbon atoms;

(4) long chain tertiary amine oxides of the formula $[R^1R^2R^3N \rightarrow O]$ where $R^1$ contains an alkyl, alkenyl or monohydroxy alkyl radical of from about 8 to about 18 carbon atoms, from 0 to about 10 ethylene oxide moieties, and from 0 to about 1 glyceryl moiety, and $R^2$ and $R^3$ contain from about 1 to about 3 carbon atoms and from 0 to about 1 hydroxy group, e.g., methyl, ethyl, propyl, hydroxyethyl, or hydroxypropyl radicals;

(5) long chain tertiary phosphine oxides of the formula $[RR'R''P \rightarrow O]$ where R contains an alkyl, alkenyl or monohydroxyalkyl radical ranging from about 8 to about 18 carbon atoms in chain length, from 0 to about 10 ethylene oxide moieties and from 0 to 1 glyceryl moieties and R' and R'' are each alkyl or monohydroxyalkyl groups containing from about 1 to about 3 carbon atoms;

(6) long chain dialkyl sulfoxides containing one short chain alkyl or hydroxy alkyl radical of from 1 to about 3 carbon atoms (usually methyl) and one long hydrophobic chain which include alkyl, alkenyl, hydroxy alkyl, or keto alkyl radicals containing from about 8 to about 20 carbon atoms, from 0 to about 10 ethylene oxide moieties and from 0 to 1 glyceryl moieties;

(7) alkyl polysaccharide (APS) surfactants (e.g. alkyl polyglycosides), including APS surfactants having a hydrophobic group with about 6 to about 30 carbon atoms and a polysaccharide (e.g., polyglycoside) as the hydrophilic group; optionally, there can be a polyalkylene-oxide group joining the hydrophobic and hydrophilic moieties; and the alkyl group (i.e., the hydrophobic moiety) can be saturated or unsaturated, branched or unbranched, and unsubstituted or substituted (e.g., with hydroxy or cyclic rings); a preferred material is alkyl polyglucoside, which is commercially available from Henkel, ICI Americas, and Seppic; and (8) polyoxyethylene alkyl ethers such as those of the formula $RO(CH_2CH_2O)_nH$ and polyethylene glycol (PEG) glyceryl fatty esters, such as those of the formula $R(O)OCH_2CH(OH)CH_2(OCH_2CH_2)_nOH$, wherein n is from 1 to about 200, preferably from about 20 to about 100, and R is an alkyl having from about 8 to about 22 carbon atoms. polyethylene glycol derivatives of glycerides as described in the above (8) useful herein include derivatives of mono-, di- and tri-glycerides and mixtures thereof. One class of polyethylene glycol derivatives of glycerides suitable herein is those which conform to the general formula (1):

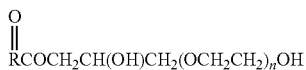

wherein n, the degree of ethoxylation, is from about 4 to about 200, preferably from about 5 to about 150, more preferably from about 20 to about 120, and wherein R comprises an aliphatic radical having from about 5 to about 25 carbon atoms, preferably from about 7 to about 20 carbon atoms. Suitable polyethylene glycol derivatives of glycerides can be polyethylene glycol derivatives of hydrogenated castor oil. Such polyethylene glycol derivatives of hydrogenated castor oil include, for example, PEG-20 hydrogenated castor oil, PEG-30 hydrogenated castor oil, PEG-40 hydrogenated castor oil, PEG-45 hydrogenated castor oil, PEG-50 hydrogenated castor oil, PEG-54 hydrogenated castor oil, PEG-55 hydrogenated castor oil, PEG-60 hydrogenated castor oil, PEG-80 hydrogenated castor oil, and PEG-100 hydrogenated castor oil.

Other suitable polyethylene glycol derivatives of glycerides can be polyethylene glycol derivatives of stearic acid. Such polyethylene glycol derivatives of stearic acid include, for example, PEG-30 stearate, PEG-40 stearate, PEG-50 stearate, PEG-75 stearate, PEG-90 stearate, PEG-100 stearate, PEG-120 stearate, and PEG-150 stearate.

Ethylene glycol ethers of fatty alcohols, as described in the above (3) or (8), useful herein include any ethylene glycol ethers of fatty alcohols which are suitable for use in a hair conditioning composition. No limiting examples of the ethylene glycol ethers of fatty alcohols include; the ceteth series of compounds such as ceteth-1 through ceteth-45, preferably ceteth-7 through ceteth-20; the isoceteth series of compounds such as isoceteth-20; the steareth series of compounds such as steareth-1 through 100; ceteareth 1 through ceteareth-50; the laureth series of compounds, preferably laureth-7 through Laureth-12; the pareth series of compounds, preferably pareth-9 through pareth-15; propylene glycol ethers of the above ceteth, steareth, ceteareth, and laureth series of compounds, such propylene glycol ethers of ceteth series of compounds including, for example, PPG-5-Ceteth-20; polyoxyethylene ethers or polyoxyethylene-polyoxypropylene ethers of branched alcohols, such branched alcohols including, for example, octyldodecyl alcohol, decyltetradecyl alcohol, dodecylpentadecyl alcohol, hexyldecyl alcohol, and isostearyl alcohol, and such polyoxyethylene-polyoxypropylene ethers of branched alcohols including, for example, POE(20)POP(6) decyltetradecyl ether; and mixtures thereof.

Other nonionic surfactants useful herein include, for example, polysorbates such as polysorbate-20 (POE(20) sorbitan monolaurate) having HLB value of 16.7, polysorbate-21 (POE(4) sorbitan monolaurate) having HLB value of 13.3, polysorbate-40 (POE(20) sorbitan monopalmitate) having HLB value of 15.6, polysorbate-60 (POE(20) sorbitan monostearate) having HLB value of 14.9, polysorbate-61 (POE(4) sorbitan monostearate) having HLB value of 9.6, polysorbate-80 (POE(20)sorbitan monooleate) having HLB value of 15.0, and polysorbate-81 (POE(4) sorbitan monooleate) having HLB value of 10.0.

In one embodiment, one or more nonionic surfactants are selected from the group consisting of PEG-40 hydrogenated castor oil, steareth-2, steareth-20, polysorbate 60, polyclyceryl-3 stearate, glyceryl stearate citrate, and a mixture thereof.

In some instances, the one or more nonionic surfactants includes PEG-40 hydrogenated castor oil.

The total amount of the one or more nonionic surfactants in the hair styling composition, if present, will vary. In various embodiments, the hair styling composition includes about 0.01 to about 10 wt. % of the one or more nonionic surfactants, based on a total weight of the hair styling composition. In further embodiments, the hair styling composition includes about 0.01 to about 8 wt. %, about 0.01 to about 6 wt. %, about 0.01 to about 5 wt. %, about 0.01 to about 3 wt. %, about 0.05 to about 10 wt. %, about 0.05 to about 8 wt. %, about 0.05 to about 6 wt. %, about 0.05 to about 5 wt. %, about 0.05 to about 3 wt. %, about 0.1 to about 10 wt. %, about 0.1 to about 8 wt. %, about 0.1 to about 6 wt. %, about 0.1 to about 5 wt. %, about 0.1 to about 3 wt. %, based on a total weight of the hair styling composition.

(j) Additional Fatty Compounds

The hair styling compositions may optionally include or exclude (or be essentially free from) on or more additional fatty compounds. Additional fatty compounds are compounds other than the: (a) one or more fatty amides, fatty alkanolamides, and/or alkoxylated fatty amides; (b) one or more non-hydroxy substituted fatty acids; and (c) one or more hydroxy substituted fatty acids. In various embodiments, the hair styling composition is free or essentially free from additional fatty compounds.

Non-limiting examples of additional fatty compounds fatty alcohols, fatty alcohol derivatives, fatty acid derivatives (such as alkoxylated fatty acids or polyethylene glycol esters of fatty acids or propylene glycol esters of fatty acids or butylene glycol esters of fatty acids or esters of neopentyl glycol and fatty acids or polyglycerol/glycerol esters of fatty acids or glycol diesters or diesters of ethylene glycol and fatty acids or esters of fatty acids and fatty alcohols, esters of short chain alcohols and fatty acids), esters of fatty alcohols, waxes, triglyceride compounds, lanolin, and a mixture thereof.

Fatty alcohols useful herein include those having from about 10 to about 30 carbon atoms, from about 12 to about 22 carbon atoms, and from about 16 to about 22 carbon atoms. These fatty alcohols can be straight or branched chain alcohols and can be saturated or unsaturated. Nonlimiting examples of fatty alcohols include decyl alcohol, undecyl alcohol, dodecyl, myristyl, cetyl alcohol, stearyl alcohol, isostearyl alcohol, isocetyl alcohol, behenyl alcohol, linalool, oleyl alcohol, cholesterol, cis4-t-butylcyclohexanol, myricyl alcohol and a mixture thereof. In some cases, the fatty alcohols are those selected from the group consisting of cetyl alcohol, stearyl alcohol, isostearyl alcohol, oleyl alcohol, and a mixture thereof.

Fatty alcohol derivatives include alkyl ethers of fatty alcohols, alkoxylated fatty alcohols, alkyl ethers of alkoxylated fatty alcohols, esters of fatty alcohols and a mixture thereof. Nonlimiting examples of fatty alcohol derivatives include materials such as methyl stearyl ether; 2-ethylhexyl dodecyl ether; stearyl acetate; cetyl propionate; the ceteth series of compounds such as ceteth-1 through ceteth-45, which are ethylene glycol ethers of cetyl alcohol, wherein the numeric designation indicates the number of ethylene glycol moieties present; the steareth series of compounds such as steareth-1 through 10, which are ethylene glycol ethers of steareth alcohol, wherein the numeric designation indicates the number of ethylene glycol moieties present; ceteareth 1 through ceteareth-10, which are the ethylene glycol ethers of ceteareth alcohol, i.e. a mixture of fatty alcohols containing predominantly cetyl and stearyl alcohol, wherein the numeric designation indicates the number of ethylene glycol moieties present; C1-C30 alkyl ethers of the ceteth, steareth, and ceteareth compounds just described; polyoxyethylene ethers of branched alcohols such as octyldodecyl alcohol, dodecylpentadecyl alcohol, hexyldecyl alcohol, and isostearyl alcohol; polyoxyethylene ethers of behenyl alcohol; PPG ethers such as PPG-9-steareth-3, PPG-11 stearyl ether, PPG8-ceteth-1, and PPG-10 cetyl ether; and a mixture thereof.

Non-limiting olyglycerol esters of fatty acids include those of the following formula:

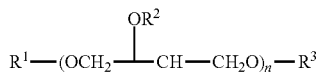

wherein the average value of n is about 3 and $R^1$, $R^2$ and $R^3$ each may independently be a fatty acid moiety or hydrogen, provided that at least one of $R^1$, $R^2$, and $R^3$ is a fatty acid moiety. For instance, $R^1$, $R^2$ and $R^3$ may be saturated or unsaturated, straight or branched, and have a length of $C_1$-$C_{40}$, $C_1$-$C_{30}$, $C_1$-$C_{25}$, or $C_1$-$C_{20}$, $C_1$-$C_{16}$, or $C_1$-$C_{10}$. For example, nonionic polyglycerol esters of fatty acids include polyglyceryl-5 laurate, The fatty acid derivatives are defined herein to include fatty acid esters of the fatty alcohols as defined above, fatty acid esters of the fatty alcohol derivatives as defined above when such fatty alcohol derivatives have an esterifiable hydroxyl group, fatty acid esters of alcohols other than the fatty alcohols and the fatty alcohol derivatives described above, hydroxy-substituted fatty acids, and a mixture thereof. Nonlimiting examples of fatty acid derivatives include ricinoleic acid, glycerol monostearate, 12-hydroxy stearic acid, ethyl stearate, cetyl stearate, cetyl palmitate, polyoxyethylene cetyl ether stearate, polyoxyethylene stearyl ether stearate, polyoxyethylene lauryl ether stearate, ethyleneglycol monostearate, polyoxyethylene monostearate, polyoxyethylene distearate, propyleneglycol monostearate, propyleneglycol distearate, trimethylolpropane distearate, sorbitan stearate, polyglyceryl stearate, dimethyl sebacate, PEG-15 cocoate, PPG-15 stearate, glyceryl monostearate, glyceryl distearate, glyceryl tristearate, PEG-8 laurate, PPG-2 isostearate, PPG-9 laurate, and a mixture thereof. Preferred for use herein are glycerol monostearate, 12-hydroxy stearic acid, and a mixture thereof.

In some cases, the one or more additional fatty compounds may be one or more high melting point fatty compounds. A high melting point fatty compound is a fatty compound having a melting point of 25° C. or higher. Even higher melting point fatty compounds may also be used, for example, fatty compounds having a melting point of 40° C. or higher, 45° C. or higher, 50° C. or higher. The high melting point fatty compounds may be selected from fatty alcohols, fatty alcohol derivatives, fatty acid derivatives, and mixtures thereof. Nonlimiting examples of the high melting point compounds are found in International Cosmetic Ingredient Dictionary, Fifteenth Edition, 2014, which is incorporated herein by reference in its entirety. Non-limiting examples of high melting point fatty compounds include fatty alcohols such as, for example, cetyl alcohol (having a melting point of about 56° C.), stearyl alcohol (having a melting point of about 58-59° C.), behenyl alcohol (having a melting point of about 71° C.), and mixtures thereof. These compounds are known to have the above melting point. However, they often have lower melting points when supplied, since such supplied products are often mixtures of fatty alcohols having alkyl chain length distribution in which the main alkyl chain is cetyl, stearyl or behenyl group.

The total amount of the one or more additional fatty compounds, if present, will vary. Nonetheless, in various embodiments, the hair styling composition includes about 0.01 to about 10 wt. % of the one or more additional fatty compounds, based on a total weight of the hair styling composition. In further embodiments, the hair treatment composition includes about 0.01 to about 8 wt. %, about 0.01 to about 6 wt. %, about 0.01 to about 5 wt. %, about 0.01 to about 3 wt. %, about 0.05 to about 10 wt. %, about 0.05 to about 8 wt. %, about 0.05 to about 6 wt. %, about 0.05 to about 5 wt. %, about 0.05 to about 3 wt. %, about 0.1 to about 10 wt. %, about 0.1 to about 8 wt. %, about 0.1 to about 6 wt. %, about 0.1 to about 5 wt. %, about 0.1 to about 3 wt. % of the one or more additional fatty compounds, based on a total weight of the hair styling composition.

(k) Thickening Agents

The hair styling composition optionally include or exclude (or are essentially free from) one or more thickening agents. Thickening agents may be referred to as "thickeners" or "viscosity modifying agents." Thickening agents are typically included to increase the viscosity of the cosmetic compositions.

Nonlimiting examples of thickening agents include xanthan gum, guar gum, biosaccharide gum, cellulose, acacia seneca gum, sclerotium gum, agarose, pechtin, gellan gum, hyaluronic acid. Additionally, the one or more thickening agents may include polymeric thickening agents selected from the group consisting of ammonium polyacryloyldimethyl taurate, ammonium acryloyldimethyltaurate/VP copolymer, sodium polyacrylate, acrylates copolymers, polyacrylamide, carbomer, and acrylates/C10-30 alkyl acrylate crosspolymer. In some cases, the composition includes ammonium polyacryloyldimethyl taurate and/or sodium polyacrylate.

Particular types of thickening agents that may be mentioned include the following:

Carboxylic acid or carboxylate based homopolymer or co-polymer, which can be linear or crosslinked:

These polymers contain one or more monomers derived from acrylic acid, substituted acrylic acids, and salts and esters of these acrylic acids (acrylates) and the substituted acrylic acids. Commercially available polymers include those sold under the trade names CARBOPOL, ACRYSOL, POLYGEL, SOKALAN, CARBOPOL ULTREZ, and POLYGEL. Examples of commercially available carboxylic acid polymers include the carbomers, which are homopolymers of acrylic acid crosslinked with allyl ethers of sucrose or pentaerytritol. The carbomers are available as the CARBOPOL 900 series from B.F. Goodrich (e.g., CARBOPOL 954). In addition, other suitable carboxylic acid polymeric agents include ULTREZ 10 (B.F. Goodrich) and copolymers of C10-30 alkyl acrylates with one or more monomers of acrylic acid, methacrylic acid, or one of their short chain (i.e., C1-4 alcohol) esters, wherein the crosslinking agent is an allyl ether of sucrose or pentaerytritol. These copolymers are known as acrylates/C10-C30 alkyl acrylate crosspolymers and are commercially available as CARBOPOL 1342, CARBOPOL 1382, PEMULEN TR-1, and PEMULEN TR-2, from B.F. Goodrich.

Other suitable carboxylic acid or carboxylate polymeric agents include copolymers of acrylic acid and alkyl C5-C10 acrylate, copolymers of acrylic acid and maleic anhydride, and polyacrylate crosspolymer-6. Polyacrylate Crosspolymer-6 is available in the raw material known as SEPIMAX ZEN from Seppic.

Another suitable carboxylic acid or carboxylate polymeric agent includes acrylamidopropyltrimonium chloride/acrylates copolymer, a cationic acrylates copolymer (or a quaternary ammonium compound), available as a raw material known under the tradename of SIMULQUAT HC 305 from Seppic.

In certain embodiments, the carboxylic acid or carboxylate polymer thickening agents useful herein are those selected from carbomers, acrylates/C10-C30 alkyl acrylate crosspolymers, polyacrylate crosspolymer-6, acrylamidopropyltrimonium chloride/acrylates copolymer, and mixtures thereof.

Polyquaternium Compounds:

Non-limiting examples, include polyquaternium-1, polyquaternium-2, polyquaternium-3, polyquaternium-4, polyquaternium-5, polyquaternium-6, polyquaternium-7, polyquaternium-8, polyquaternium-9, polyquaternium-10, polyquaternium-11, polyquaternium-12, polyquaternium-13, polyquaternium-14, polyquaternium-15, polyquaternium-16, polyquaternium-17, polyquaternium-18, polyquaternium-19, polyquaternium-20, polyquaternium-21, polyquaternium-22, polyquaternium-23, polyquaternium-24, polyquaternium-25, polyquaternium-26, polyquaternium-27, polyquaternium-28, polyquaternium-29, polyquaternium-30, polyquaternium-40, polyquaternium-41, polyquaternium-42, polyquaternium-43, polyquaternium-44, polyquaternium-45, polyquaternium-46, polyquaternium-47, polyquaternium-48, polyquaternium-49, polyquaternium-50, polyquaternium-51, polyquaternium-52, polyquaternium-53, polyquaternium-54, polyquaternium-55, polyquaternium-56, polyquaternium-57, polyquaternium-58, polyquaternium-59, polyquaternium-60, polyquaternium-61, polyquaternium-62, polyquaternium-63, polyquaternium-64, polyquaternium-65, polyquaternium-66, polyquaternium-67, etc. In some cases, preferred polyquaternium compounds include polyquaternium-10, polyquaternium-11, polyquaternium-67, and a mixture thereof.

Celluloses:

Non-limiting examples of celluloses include cellulose, carboxymethyl hydroxyethylcellulose, cellulose acetate propionate carboxylate, hydroxyethylcellulose, hydroxyethyl ethylcellulose, hydroxypropylcellulose, hydroxypropyl methylcellulose, methyl hydroxyethylcellulose, microcrystalline cellulose, sodium cellulose sulfate, and mixtures thereof. In some instances, the cellulose is selected from water soluble cellulose derivatives (for example, carboxymethyl cellulose, methyl cellulose, methylhydroxypropyl cellulose, hydroxyethyl cellulose, hydroxypropyl cellulose, cellulose sulfate sodium salt). Furthermore, in some instance, the cellulose is preferably hydroxypropylcellulose (HPC).

Polyvinylpyrrolidone (PVP) and Co-Polymers:

Non-limiting examples include Polyvinylpyrrolidone (PVP), Polyvinylpyrrolidone(PVP)/vinyl acetate copolymer (PVP/VA copolymer), polyvinylpyrrolidone (PVP)/eicosene copolymer, PVP/hexadecene copolymer, etc. Commercially available polyvinylpyrrolidone includes LUVISKOL K30, K85, K90 available from BASF. Commerically available copolymers of vinylpyrrolidone and vinylacetate include LUVISKOL VA37, VA64 available from BASF; copolymers of vinylpyrrolidone, methacrylamide, and vinylimidazole (INCI: VP/Methacrylamide/Vinyl Imidazole Copolymer) is commercially available as LUVISET from BASF. In some instances, PVP and PVP/VA copolymer are preferred.

Sucrose Esters:

Non-limiting examples include sucrose palmitate, sucrose cocoate, sucrose monooctanoate, sucrose monodecanoate, sucrose mono- or dilaurate, sucrose monomyristate, sucrose mono- or dipalmitate, sucrose mono- and distearate, sucrose mono-, di- or trioleate, sucrose mono- or dilinoleate, sucrose pentaoleate, sucrose hexaoleate, sucrose heptaoleate or sucrose octooleate, and mixed esters, such as sucrose palmitate/stearate, and mixtures thereof.

Gums:

Non-limiting examples of gums include gum arabic, tragacanth gum, karaya gum, guar gum, gellan gum, tara gum, locust bean gum, tamarind gum, xanthan gum, locust bean gum, Seneca gum, sclerotium gum, gellan gum, etc.

The total amount of the one or more thickening agents, if present, will vary.

Nonetheless, in various embodiments, the hair styling composition includes about 0.01 to about 8 wt. % of the one or more thickening agents, based on a total weight of the hair styling composition. In further embodiments, the hair treatment composition includes about 0.01 to about 6 wt. %, about 0.01 to about 5 wt. %, about 0.01 to about 3 wt. %, about 0.05 to about 8 wt. %, about 0.05 to about 6 wt. %, about 0.05 to about 5 wt. %, about 0.05 to about 3 wt. %, about 0.1 to about 8 wt. %, about 0.1 to about 6 wt. %, about 0.1 to about 5 wt. %, about 0.1 to about 3 wt. % of the one or more thickening agents, based on a total weight of the hair styling composition.

(l) Miscellaneous Ingredients

The hair styling composition optionally includes or excludes (or is essentially free from) one or more miscellaneous ingredients. In a preferred embodiment, the hair styling composition includes one or more miscellaneous ingredients. Miscellaneous ingredients are ingredients that are compatible with the hair coloring compositions and do not disrupt or materially affect the basic and novel properties of the compositions. Nonlimiting examples of ingredients include preservatives, fragrances, pH adjusters, salts, chelating agents, buffers, antioxidants, flavonoids, vitamins, botanical extracts, UV filtering agents, proteins, protein hydrolysates, and/or isolates, fillers (e.g., organic and/or inorganic fillers such as talc, calcium carbonate, silica, etc.) composition colorants, etc. In various embodiments, the miscellaneous ingredients are chosen from preservatives, fragrances, pH adjusters, salts, chelating agents, buffers, composition colorants, and mixtures thereof. In the context of the instant disclosure, a "composition colorant" is a compound that colors the composition but does not have an appreciable coloring effect on hair. In other words, the composition colorant is included to provide a coloring to the composition for aesthetic appeal but is not intended to impart coloring properties to hair. Styling gels, for example, can be found in a variety of different colors (e.g., light blue, light pink, etc.) yet application of the styling gel to hair does not visibly change the color of the hair.

In addition to the above, the following components described as optional component throughout the disclosure are also miscellaneous ingredients if not expressly set forth as an independent component of the hair styling composition: alkoxylated polyol esters (e), water soluble organic solvents (f), film-forming polymers (j), cationic conditioning polymers (h), surfactants (nonionic (i), anionic, cationic, and amphoteric/zwitterionic), additional fatty compounds (j), or a combination thereof. Thus, the term "miscellaneous ingredient" is understood as a catch-all phrase representing additional components that may optionally be present in amounts designated for the miscellaneous ingredients.

The amount of the one or more miscellaneous ingredients in the hair styling composition, if present, will vary. Nonetheless, in various embodiments, the hair styling composition includes about 0.01 to about 8 wt. % of the one or more miscellaneous ingredients, based on a total weight of the hair styling composition. In further embodiments, the hair styling composition includes about 0.01 to about 6 wt. %, about 0.01 to about 5 wt. %, about 0.01 to about 3 wt. %, about 0.05 to about 8 wt. %, about 0.05 to about 6 wt. %, about 0.05 to about 5 wt. %, about 0.05 to about 3 wt. %, based on a total weight of the hair styling composition.

Forms

The hair styling composition may be in a variety of different forms, for example, a wax, a gel, a paste, a clay, a pomade, etc. The compositions typically have a more solid-like or thick consistency at rest (or when subjected to only light shear force) but when subjected to more vigorous physical manipulation (when subjected to stronger shear force such as rubbing product in palms or hands) the compositions transform into a more liquid-like consistency. The liquid-like consistency eases application of the hair styling composition to the hair. After styling the hair, the hair styling compositions returns to its more solid-like or thick consistency, which provides improved durability and hold to the hair style.

The viscosity of the hair styling compositions can be determined according to known methods for measuring viscosity. For instance, the viscosity is measured with a Discovery HR-2 rheometer from TA Instruments at 25° C. using 40 mm parallel sand blasted plates, a 300 µm gap, and a shear range from 0.1/s to 100/s.

The viscosity of the hair styling composition will vary. Nonetheless, in various embodiments, the viscosity of the hair styling composition is about 1 to about 200 Pas, at a shear rate of 4/s at 25° C. In further embodiments, the viscosity of the hair styling composition is about 1 to about 150 Pas, about 1 to about 100 Pas, about 1 to about 75 Pas, about 1 to about 50 Pas, about 2 to about 50 Pas, or about 5 to about 50 Pas at a shear rate of 4/s at 25° C.

EMBODIMENTS

In various embodiments, the hair styling compositions of the instant disclosure comprise or consist of:
 (a) about 1 to about 15 wt. %, preferably about 2 to about 12 wt. %, more preferably about 3 to about 8 wt. % of one or more fatty amides, fatty alkanolamides, and/or alkoxylated fatty amides, preferably one or more fatty alkanolamides, in particular, one or more fatty alkanolamides selected from cocamide MEA, cocamide DEA, soyamide DEA, lauramide DEA, oleamide MIPA, stearamide MEA, myristamide DEA, stearamide DEA, oleylamide DEA, tallowamide DEA lauramide MIPA, tallowamide MEA, isostearamide DEA, isostearamide MEA, or a mixture thereof, more preferably the one or more fatty alkanolamides is cocamide MEA;
 (b) about 1 to about 12 wt. %, preferably about 2 to about 10 wt. %, more preferably about 3 to about 8 wt. % of one or more non-hydroxy substituted fatty acids, preferably one or more non-hydroxy substituted fatty acids selected from oleic acid, lauric acid, palmitic acid, myristic acid, stearic acid, linoleic acid, capric acid, and a combination thereof, more preferably selected from oleic acid, lauric acid, or a combination thereof;
 (c) about 1 to about 10 wt. %, preferably about 1 to about 8 wt. %, more preferably about 1.5 to about 6 wt. % of one or more hydroxy substituted fatty acids, preferably one or more hydroxy substituted fatty acids selected from 12-hydroxystearic acid, 9,10-dihydroxyoctadecanoic acid, 9,10,18-trihydroxyoctadecanoic acid, lesquerolic acid, 15-hydroxyhexadecanoic acid, isoricinoleic acid, densipolic acid, 14-hydroxy-eicosa-cis-11-cis-17-dienoic acid, 2-hydroxyoleic acid, 2-hydroxylinoleic acid, 18-hydroxystearic acid, 15-hydroxylinoleic acid, and a combination thereof, more preferably, wherein the one or more hydroxy substituted fatty acid is hydroxystearic acid;
 (d) about 70 to about 95 wt. %, preferably about 70 to about 90 wt. %, more preferably about 75 to about 90 wt. % of one or more low-polar oils, preferably wherein the one or more low-polar oils are hydrocarbon-based oils (non-silicone), even more preferably the one or more low-polar oils are natural oils, in particular vegetable oils, for example, selected from sunflower oil, canola oil, soybean oil, corn oil, peanut oil, palm oil, castor bean oil, cotton oil, lesquerella oil, crambe oil, safflower oil, and mixtures thereof;
 (e) optionally, about 0.1 to about 10 wt. %, preferably about 0.5 to about 8 wt. %, more preferably about 1 to about 5 wt. % of one or more alkoxylated polyol esters, preferably one or more alkoxylated polyol esters selected from pegylated derivatives of propylene glycol oleate, propylene glycol caprylate/caprate, propylene glycol cocoate, propylene glycol stearate, and a mixture thereof, more preferably the one or more alkoxylated polyol esters is selected from PEG-55 propylene glycol oleate, PEG-6 propylene glycol caprylate/caprate, PEG-8 propylene glycol cocoate, PEG-25 propylene glycol stearate, and PEG-120 propylene glycol stearate, or a mixture thereof, in particular, PEG-55 propylene glycol oleate; and
 (f) optionally, about 0.1 to about 10 wt. %, preferably about 0.5 to about 8 wt. %, more preferably about 1 to about 6 wt. % of one or more water-soluble organic solvents, preferably one or more water-soluble organic solvents selected from C1-6 mono-alcohols, polyols (polyhydric alcohols), glycols, and a mixture thereof, more preferably selected from ethyl alcohol, isopropyl alcohol, propyl alcohol, benzyl alcohol, phenylethyl alcohol, ethylene glycol, propylene glycol, butylene glycol, pentylene glycol, hyxelen glycol, dipropylene glycol, or a combination thereof; and
 (g) optionally, about 0.01 to about 8 wt. %, preferably about 0.05 to about 6 wt. %, more preferably about 0.1 to about 5 wt. % of one or more miscellaneous ingredients, preferably selected from preservatives, fragrances, pH adjusters, salts, chelating agents, buffers, antioxidants, flavonoids, vitamins, botanical extracts, UV filtering agents, proteins, protein hydrolysates, and/or isolates, fillers (organic and/or inorganic fillers such as talc, calcium carbonate, silica, etc.), or a combination thereof;
 wherein the composition comprises less than 2 wt. % of water, the composition exhibits non-Newtonian shear thinning behavior and,
 all weight percentages are based on a total weight of the composition.

In various embodiments, the hair styling composition above is free or essentially free from film-forming polymers. In an embodiment, the hair styling composition is free or essentially free from nonionic film-forming polymers. In another embodiment, the hair styling composition is free or essentially free from amphoteric film-forming polymers.

In various embodiments, the hair styling composition above is free or essentially free from cationic conditioning polymers.

In various embodiments, the hair styling composition above is free or essentially free from anionic surfactants. In various embodiments, the hair styling composition above is free or essentially free from cationic surfactants. In various embodiments, the hair styling composition above is free or essentially free from amphoteric/zwitterionic surfactants. In various embodiments, the hair styling composition above is free or essentially free from nonionic surfactants. In various embodiments, the hair styling composition above is free or essentially free from surfactants (anionic, cationic, nonionic, and amphoteric/zwitterionic surfactants).

In various embodiments, the hair styling composition above is free or essentially free from silicones. The term "silicones" is a generic term referring to a class of synthetic polymers that are based on a framework of alternating silicon and oxygen (siloxane) bonds with at least one organic group attached to the silicon atom via a direct carbon-silicon bond.

In various embodiments, the hair styling composition above is free or essentially free from thickening agents.

In various embodiments, the hair styling composition above is free or essentially free from polyquaternium compounds.

In various embodiments, the hair styling composition above is free or essentially free from additional fatty compounds.

In various embodiments, the hair styling composition is in the form of a wax, a gel, a paste, a clay, or a pomade.

In various embodiments, the hair styling compositions of the instant disclosure comprise or consist of:
  (a) about 1 to about 15 wt. %, preferably about 2 to about 12 wt. %, more preferably about 3 to about 8 wt. % of one or more fatty alkanolamides, selected from cocamide MEA, cocamide DEA, soyamide DEA, lauramide DEA, oleamide MIPA, stearamide MEA, myristamide DEA, stearamide DEA, oleylamide DEA, tallowamide DEA lauramide MIPA, tallowamide MEA, isostearamide DEA, isostearamide MEA, or a mixture thereof, more preferably the one or more fatty alkanolamides is cocamide MEA;
  (b) about 1 to about 12 wt. %, preferably about 2 to about 10 wt. %, more preferably about 3 to about 8 wt. % of one or more non-hydroxy substituted fatty acids selected from oleic acid, lauric acid, palmitic acid, myristic acid, stearic acid, linoleic acid, capric acid, and a combination thereof, more preferably selected from oleic acid, lauric acid, or a combination thereof;
  (c) about 1 to about 10 wt. %, preferably about 1 to about 8 wt. %, more preferably about 1.5 to about 6 wt. % of one or more hydroxy substituted fatty acids selected from 12-hydroxystearic acid, 9,10-dihydroxyoctadecanoic acid, 9,10,18-trihydroxyoctadecanoic acid, lesquerolic acid, 15-hydroxyhexadecanoic acid, isoricinoleic acid, densipolic acid, 14-hydroxy-eicosa-cis-11-cis-17-dienoic acid, 2-hydroxyoleic acid, 2-hydroxylinoleic acid, 18-hydroxystearic acid, 15-hydroxylinoleic acid, and a combination thereof, more preferably, wherein the one or more hydroxy substituted fatty acid is hydroxystearic acid;
  (d) about 70 to about 95 wt. %, preferably about 70 to about 90 wt. %, more preferably about 75 to about 90 wt. % of one or more low-polar hydrocarbon-based oils selected from natural oils, in particular vegetable oils, for example, selected from sunflower oil, canola oil, soybean oil, corn oil, peanut oil, palm oil, castor bean oil, cotton oil, *lesquerella* oil, *crambe* oil, safflower oil, and mixtures thereof;
  (e) about 0.1 to about 10 wt. %, preferably about 0.5 to about 8 wt. %, more preferably about 1 to about 5 wt. % of one or more alkoxylated polyol esters, preferably one or more alkoxylated polyol esters selected from pegylated derivatives of propylene glycol oleate, propylene glycol caprylate/caprate, propylene glycol cocoate, propylene glycol stearate, and a mixture thereof, more preferably the one or more alkoxylated polyol esters is selected from PEG-55 propylene glycol oleate, PEG-6 propylene glycol caprylate/caprate, PEG-8 propylene glycol cocoate, PEG-25 propylene glycol stearate, and PEG-120 propylene glycol stearate, or a mixture thereof, in particular, PEG-55 propylene glycol oleate; and
  (f) about 0.1 to about 10 wt. %, preferably about 0.5 to about 8 wt. %, more preferably about 1 to about 6 wt. % of one or more water-soluble organic solvents selected from C1-6 mono-alcohols, polyols (polyhydric alcohols), glycols, and a mixture thereof, more preferably selected from ethyl alcohol, isopropyl alcohol, propyl alcohol, benzyl alcohol, phenylethyl alcohol, ethylene glycol, propylene glycol, butylene glycol, pentylene glycol, hyxelen glycol, dipropylene glycol, or a combination thereof; and
  (g) about 0.01 to about 8 wt. %, preferably about 0.05 to about 6 wt. %, more preferably about 0.1 to about 5 wt. % of one or more miscellaneous ingredients selected from preservatives, fragrances, pH adjusters, salts, chelating agents, buffers, antioxidants, flavonoids, vitamins, botanical extracts, UV filtering agents, proteins, protein hydrolysates, and/or isolates, fillers (organic and/or inorganic fillers such as talc, calcium carbonate, silica, etc.), or a combination thereof;
    wherein the composition comprises less than 2 wt. % of water, the composition exhibits non-Newtonian shear thinning behavior and,
    all weight percentages are based on a total weight of the composition.

In various embodiments, the hair styling composition above is free or essentially free from film-forming polymers. In an embodiment, the hair styling composition is free or essentially free from nonionic film-forming polymers. In another embodiment, the hair styling composition is free or essentially free from amphoteric film-forming polymers.

In various embodiments, the hair styling composition above is free or essentially free from cationic conditioning polymers.

In various embodiments, the hair styling composition above is free or essentially free from anionic surfactants. In various embodiments, the hair styling composition above is free or essentially free from cationic surfactants. In various embodiments, the hair styling composition above is free or essentially free from amphoteric/zwitterionic surfactants. In various embodiments, the hair styling composition above is free or essentially free from nonionic surfactants. In various embodiments, the hair styling composition above is free or essentially free from surfactants (anionic, cationic, nonionic, and amphoteric/zwitterionic surfactants).

In various embodiments, the hair styling composition above is free or essentially free from silicones. The term "silicones" is a generic term referring to a class of synthetic polymers that are based on a framework of alternating silicon and oxygen (siloxane) bonds with at least one organic group attached to the silicon atom via a direct carbon-silicon bond.

In various embodiments, the hair styling composition above is free or essentially free from thickening agents.

In various embodiments, the hair styling composition above is free or essentially free from polyquaternium compounds.

In various embodiments, the hair styling composition above is free or essentially free from additional fatty compounds.

In various embodiments, the hair styling composition is in the form of a wax, a gel, a paste, a clay, or a pomade.

In other embodiments, the hair styling compositions of the instant disclosure consist of:
- (a) about 1 to about 15 wt. %, preferably about 2 to about 12 wt. %, more preferably about 3 to about 8 wt. % of one or more fatty alkanolamides, selected from cocamide MEA, cocamide DEA, soyamide DEA, lauramide DEA, oleamide MIPA, stearamide MEA, myristamide DEA, stearamide DEA, oleylamide DEA, tallowamide DEA lauramide MIPA, tallowamide MEA, isostearamide DEA, isostearamide MEA, or a mixture thereof, more preferably the one or more fatty alkanolamides is cocamide MEA;
- (b) about 1 to about 12 wt. %, preferably about 2 to about 10 wt. %, more preferably about 3 to about 8 wt. % of one or more non-hydroxy substituted fatty acids selected from oleic acid, lauric acid, palmitic acid, myristic acid, stearic acid, linoleic acid, capric acid, and a combination thereof, more preferably selected from oleic acid, lauric acid, or a combination thereof;
- (c) about 1 to about 10 wt. %, preferably about 1 to about 8 wt. %, more preferably about 1.5 to about 6 wt. % of one or more hydroxy substituted fatty acids selected from 12-hydroxystearic acid, 9,10-dihydroxyoctadecanoic acid, 9,10,18-trihydroxyoctadecanoic acid, lesquerolic acid, 15-hydroxyhexadecanoic acid, isoricinoleic acid, densipolic acid, 14-hydroxy-eicosa-cis-11-cis-17-dienoic acid, 2-hydroxyoleic acid, 2-hydroxylinoleic acid, 18-hydroxystearic acid, 15-hydroxylinoleic acid, and a combination thereof, more preferably, wherein the one or more hydroxy substituted fatty acid is hydroxystearic acid;
- (d) about 70 to about 95 wt. %, preferably about 70 to about 90 wt. %, more preferably about 75 to about 90 wt. % of one or more low-polar hydrocarbon-based oils selected from natural oils, in particular vegetable oils, for example, selected from sunflower oil, canola oil, soybean oil, corn oil, peanut oil, palm oil, castor bean oil, cotton oil, *lesquerella* oil, *crambe* oil, safflower oil, and mixtures thereof;
- (e) about 0.1 to about 10 wt. %, preferably about 0.5 to about 8 wt. %, more preferably about 1 to about 5 wt. % of one or more alkoxylated polyol esters, preferably one or more alkoxylated polyol esters selected from pegylated derivatives of propylene glycol oleate, propylene glycol caprylate/caprate, propylene glycol cocoate, propylene glycol stearate, and a mixture thereof, more preferably the one or more alkoxylated polyol esters is selected from PEG-55 propylene glycol oleate, PEG-6 propylene glycol caprylate/caprate, PEG-8 propylene glycol cocoate, PEG-25 propylene glycol stearate, and PEG-120 propylene glycol stearate, or a mixture thereof, in particular, PEG-55 propylene glycol oleate; and
- (f) about 0.1 to about 10 wt. %, preferably about 0.5 to about 8 wt. %, more preferably about 1 to about 6 wt. % of one or more water-soluble organic solvents selected from C1-6 mono-alcohols, polyols (polyhydric alcohols), glycols, and a mixture thereof, more preferably selected from ethyl alcohol, isopropyl alcohol, propyl alcohol, benzyl alcohol, phenylethyl alcohol, ethylene glycol, propylene glycol, butylene glycol, pentylene glycol, hyxelen glycol, dipropylene glycol, or a combination thereof;
- (g) optionally, about 0.01 to about 10 wt. %, preferably about 0.05 to about 8, more preferably about 0.1 to about 5 wt. % of one or more nonionic film-forming polymers, one or more amphoteric film-forming polymers, or a combination there;
- (h) optionally, about 0.01 to about 10 wt. %, preferably about 0.05 to about 8 wt. %, more preferably about 0.1 to about 5 wt. % of one or more cationic conditioning polymers;
- (i) optionally, about 0.01 to about 10 wt. %, preferably about 0.05 to about 8 wt. % more preferably about 0.1 to about 5 wt. % of one or more surfactants, preferably one or more nonionic surfactants;
- (j) optionally, about 0.01 to about 10 wt. %, preferably about 0.05 to about 8 wt. %, more preferably about 0.1 to about 5 wt. % of one or more additional fatty compounds;
- (k) optionally, about 0.01 to about 10 wt. %, preferably about 0.05 to about 8 wt. %, more preferably about 0.1 to about 5 wt. % of one or more thickening agents; and
- (j) about 0.01 to about 8 wt. %, preferably about 0.05 to about 6 wt. %, more preferably about 0.1 to about 5 wt. % of one or more miscellaneous ingredients selected from preservatives, fragrances, pH adjusters, salts, chelating agents, buffers, antioxidants, flavonoids, vitamins, botanical extracts, UV filtering agents, proteins, protein hydrolysates, and/or isolates, fillers (organic and/or inorganic fillers such as talc, calcium carbonate, silica, etc.), or a combination thereof;
  - wherein the composition comprises less than 2 wt. % of water, the composition exhibits non-Newtonian shear thinning behavior and,
  - all weight percentages are based on a total weight of the composition.

In various embodiments, the hair styling composition above is free or essentially free from film-forming polymers. In an embodiment, the hair styling composition is free or essentially free from nonionic film-forming polymers. In another embodiment, the hair styling composition is free or essentially free from amphoteric film-forming polymers.

In various embodiments, the hair styling composition above is free or essentially free from cationic conditioning polymers.

In various embodiments, the hair styling composition above is free or essentially free from anionic surfactants. In various embodiments, the hair styling composition above is free or essentially free from cationic surfactants. In various embodiments, the hair styling composition above is free or essentially free from amphoteric/zwitterionic surfactants. In various embodiments, the hair styling composition above is free or essentially free from nonionic surfactants. In various embodiments, the hair styling composition above is free or essentially free from surfactants (anionic, cationic, nonionic, and amphoteric/zwitterionic surfactants).

In various embodiments, the hair styling composition above is free or essentially free from silicones. The term "silicones" is a generic term referring to a class of synthetic polymers that are based on a framework of alternating silicon and oxygen (siloxane) bonds with at least one organic group attached to the silicon atom via a direct carbon-silicon bond.

In various embodiments, the hair styling composition above is free or essentially free from thickening agents.

In various embodiments, the hair styling composition above is free or essentially free from polyquaternium compounds.

In various embodiments, the hair styling composition above is free or essentially free from additional fatty compounds.

In various embodiments, the hair styling composition is in the form of a wax, a gel, a paste, a clay, or a pomade.

Methods of Styling Hair

The hair stylings compositions may be used in various methods for treating hair, for example, human hair, including human hair one an individual's head. For example, the hair styling compositions are useful for: (i) improving or retaining curl definition or hold of hair; (ii) styling and shaping the hair; (iii) providing hair fiber alignment and discipline; and (iv) improving the appearance of hair; wherein the methods typically comprise applying a hair styling composition disclosed herein to the hair.

In some instances, the hair styling composition is applied to the hand, for example, to the fingers, and the hands are sued to the apply the styling composition to the hair. In other words, a sufficient amount of hair styling composition may be deposited into the hands or onto the fingers, the hand may rubbed together to disperse the hair styling compositions (which provides shear stress that fluidizes the compositions), and the fingers are used to apply the hair styling composition to the hair. Upon application, the fingers/hand can be used to manipulate and style the hair.

Implementation of the present disclosure is provided by way of the following examples. The examples serve to illustrate the technology without being limiting in nature.

Viscosity was measured using a Discovery HR-2 rheometer from TA Instruments at 25° C. using 40 mm parallel sand blasted plates, a 300 μm gap, and a shear range of 0.1/s to 100/s.

As shown by Comparative Composition E, without Component (a) (cocamide MEA) and component (c) (hydroxystearic acid) the consistency of the composition is very low resulting in a liquid consistency.

Example 2

Testing for Holding Power

Inventive Composition D and Comparative Composition F were tested to determine how they impact hair with respect to styling benefits. Inventive Composition D includes a non-hydroxy substituted fatty acid (oleic and lauric acid). Comparative Composition F is identical to Inventive Composition D except is lacks a non-hydroxy substituted fatty acid. The absence of non-hydroxy substituted fatty acids is compensated for by additional low-polar oil.

Each composition was individually tested on Curl Pattern VII hair swatches. All hair swatches were initially cleansed with a standard shampoo, rinsed, and dried. 0.3 grams of Inventive Composition D or Comparative Composition F was subjected to rubbing between hands (causing shear) and subsequently applied to the hair swatches by massaging for about 20 seconds. The hair swatches were visually evaluated and then immediately placed into a humidity chamber at 25° C. and 80% relative humidity for 24 hours. After 24 hours, the hair swatches were again visually evaluated.

Upon initial application (T0) Inventive Composition D provide more curl elongation and thus more holding power (hold) than Comparative Composition F. After 24 hours in a humidity chamber Inventive Composition D continued to provide more curl elongation and thus more holding power (hold) than Comparative Composition F. In other words, Inventive Composition D imparted more hold and styling benefits to the curly hair than Comparative Composition F upon initial application and after 24 hours at 25° C. and 80% relative humidity. This demonstrates the influence of the non-hydroxy substituted fatty acid (component (b)) to the hair styling compositions.

Example 1
(Compositions)

|   |   |   | Inventive | | | | Comparative | |
|---|---|---|---|---|---|---|---|---|
|   |   |   | A | B | C | D | E | F |
| (a) | Fatty Alkanolamide | COCAMIDE MEA | 6 | 6 | 6 | 6 |   | 6 |
| (b) | Non-Hydroxy Substituted Fatty Acid | OLEIC ACID | 4 | 4 | 5 | 4 | 4 |   |
|   |   | LAURIC ACID | 1 | 1 |   | 1 | 1 |   |
| (c) | Hydroxy-Substituted Fatty Acid | HYDROXYSTEARIC ACID | 2 | 2 | 2 | 2 |   | 2 |
| (d) | Low-polar Oil | *HELIANTHUS ANNUUS* (SUNFLOWER) SEED OIL | 83.8 |   |   | 87 | 95 | 92 |
|   |   | GLYCINE SOJA (SOYBEAN) OIL |   | 83.8 | 83.8 |   |   |   |
| (e) | Alkoxylated Polyol Ester | PEG-55 PROPYLENE GLYCOL OLEATE | 1.2 | 1.2 | 1.2 |   |   |   |
| (f) | Water Soluble Solvent | PROPYLENE GLYCOL | 1.2 | 1.2 | 1.2 |   |   |   |
| (g) | Miscellaneous Ingredients | Fragrances, preservatives pH adjuster (sodium hydroxide), vegetal extracts, etc. | 0.2 | 0.2 | 0.2 |   |   |   |
|   | Water | WATER | 0.6 | 0.6 | 0.6 |   |   |   |
|   | Viscosity (shear rate of 4/s)[1] |   | 8.7 | 30.7 | 33.8 | 43.4 | 0.05 | 57.9 |

The foregoing description illustrates and describes the disclosure. Additionally, the disclosure shows and describes only the preferred embodiments but, as mentioned above, it is to be understood that it is capable to use in various other combinations, modifications, and environments and is capable of changes or modifications within the scope of the invention concepts as expressed herein, commensurate with the above teachings and/or the skill or knowledge of the relevant art. The embodiments described herein above are further intended to explain best modes known by applicant and to enable others skilled in the art to utilize the disclosure in such, or other, embodiments and with the various modifications required by the particular applications or uses thereof. Accordingly, the description is not intended to limit the invention to the form disclosed herein. Also, it is intended to the appended claims be construed to include alternative embodiments.

As used herein, the terms "comprising," "having," and "including" are used in their open, non-limiting sense.

The terms "a," "an," and "the" are understood to encompass the plural as well as the singular. Thus, the term "a mixture thereof" also relates to "mixtures thereof." Throughout the disclosure, the term "a mixture thereof" is used, following a list of elements as shown in the following example where letters A-F represent the elements: "one or more elements selected from the group consisting of A, B, C, D, E, F, and a mixture thereof." The term, "a mixture thereof" does not require that the mixture include all of A, B, C, D, E, and F (although all of A, B, C, D, E, and F may be included). Rather, it indicates that a mixture of any two or more of A, B, C, D, E, and F can be included. In other words, it is equivalent to the phrase "one or more elements selected from the group consisting of A, B, C, D, E, F, and a mixture of any two or more of A, B, C, D, E, and F."

Likewise, the term "a salt thereof" also relates to "salts thereof." Thus, where the disclosure refers to "an element selected from the group consisting of A, B, C, D, E, F, a salt thereof, and a mixture thereof," it indicates that that one or more of A, B, C, D, and F may be included, one or more of a salt of A, a salt of B, a salt of C, a salt of D, a salt of E, and a salt of F may be include, or a mixture of any two of A, B, C, D, E, F, a salt of A, a salt of B, a salt of C, a salt of D, a salt of E, and a salt of F may be included.

The salts referred to throughout the disclosure may include salts having a counter-ion such as an alkali metal, alkaline earth metal, or ammonium counterion. This list of counterions, however, is non-limiting. Appropriate counterions for the components described herein are known in the art.

The expression "one or more" means "at least one" and thus includes individual components as well as mixtures/combinations.

The term "plurality" means "more than one" or "two or more."

Other than in the operating examples, or where otherwise indicated, all numbers expressing quantities of ingredients and/or reaction conditions may be modified in all instances by the term "about," meaning within +/−5% of the indicated number.

All percentages, parts and ratios herein are based upon the total weight of the compositions of the present invention, unless otherwise indicated.

Some of the various categories of components identified may overlap. In such cases where overlap may exist and the composition includes both components (or the composition includes more than two components that overlap), an overlapping compound does not represent more than one component. For example, certain compounds may be considered both an emulsifier and a fatty compound. If a particular composition includes both an emulsifier and a fatty compound, a single compound will serve as only the emulsifier or the fatty compound (the single compound does not serve as both the emulsifier and the fatty component).

A "rinse-off" product refers to a composition that is rinsed and/or washed from the hair with water either after or during the application of the composition onto the hair, and before drying and/or styling the hair. At least a portion of the composition is removed from the hair during the rinsing and/or washing.

A "leave-on" product refers to a composition that is not rinsed and/or washed from the hair after or during application of the composition onto the hair. The composition remains on the hair during drying and/or throughout styling.

As used herein, all ranges provided are meant to include every specific range within, and combination of sub ranges between, the given ranges. Thus, a range from 1-5, includes specifically 1, 2, 3, 4 and 5, as well as sub ranges such as 2-5, 3-5, 2-3, 2-4, 1-4, etc. All ranges and values disclosed herein are inclusive and combinable. For examples, any value or point described herein that falls within a range described herein can serve as a minimum or maximum value to derive a sub-range, etc.

The hair styling composition of the instant case optionally include one or more surfactants and/or emulsifiers, for example, one or more nonionic, anionic, cationic, and/or amphoteric/zwitterionic surfactants. The term "surfactants" and "emulsifiers" include salts of the surfactants and emulsifiers even if not explicitly stated. In other words, whenever the disclosure refers to a surfactant or emulsifier, it is intended that salts are also encompassed to the extent such salts exist, even though the specification may not specifically refer to a salt (or may not refer to a salt in every instance throughout the disclosure), for example, by using language such as "a salt thereof" or "salts thereof." Sodium and potassium are common cations that form salts with surfactants and emulsifiers. However, additional cations such as ammonium ions, or alkanolammonium ions such as monoethanolammonium or triethanolammonium ions, may also form salts of surfactants.

The term "substantially free" or "essentially free" as used herein means that there is less than about 2% by weight of a specific material added to a composition, based on the total weight of the compositions. Nonetheless, the compositions may include less than about 1 wt. %, less than about 0.5 wt. %, less than about 0.1 wt. %, or none of the specified material.

All components that are positively set forth in the instant disclosure may be negatively excluded from the claims, e.g., a claimed composition may be "free," "essentially free" (or "substantially free") of one or more components that are positively set forth in the instant disclosure. As an example, the hair styling composition of the instant disclosure may optionally include one or more silicone oils or silicone containing emulsifiers. However, the hair styling compositions may be free or essentially free from silicone oils and/or silicone containing emulsifiers.

All publications and patent applications cited in this specification are herein incorporated by reference, and for any and all purposes, as if each individual publication or patent application were specifically and individually indicated to be incorporated by reference. In the event of an inconsistency between the present disclosure and any publications or patent application incorporated herein by reference, the present disclosure controls.

The invention claimed is:
1. A hair styling composition comprising:
(a) about 1 to about 15 wt. % of one or more fatty amides, fatty alkanolamides, and/or alkoxylated fatty amides;
(b) about 1 to about 12 wt. % of one or more non-hydroxy substituted fatty acids;
(c) about 1 to about 8 wt. % of one or more hydroxy substituted fatty acids; and
(d) about 70 to about 95 wt. % of one or more low-polar oils;
wherein the composition comprises less than 2 wt. % of water, the composition exhibits non-Newtonian shear thinning behavior, the composition is a wax-like consistency until subjected to shear, and all weight percentages are based on a total weight of the composition.

2. The hair styling composition of claim 1, wherein the one or more fatty amides, fatty alkanolamides, and/or alkoxylated fatty amides of (a) are selected from Cocamide, Cocamide Methyl MEA, Cocoyl Glutamic Acid, Erucamide, Lauramide, Oleamide, Palmitamide, Stearamide, Stearyl Erucamide, Behenamide DEA, Behenamide MEA, Cocamide DEA, Cocamide MEA, Cocamide MIPA, Hydroxyethyl Stearamide-MIPA, Hydroxypropyl Bisisostearamide MEA, Hydroxypropyl Bislauramide MEA, Hydroxystearamide MEA, Isostearamide DEA, Isostearamide MEA, Isostearamide MIPA, Lauramide DEA, Lauramide MEA, Lauramide MIPA, Myristamide DEA, Myristamide MEA, Myristamide MIPA, Palmamide DEA, Palmamide MEA, Palmamide MIPA, Palmitamide DEA, Palmitamide MEA, PEG-20 Cocamide MEA, Stearamide AMP, Stearamide DEA, Stearamide DEA-Distearate, Stearamide DIBA-Stearate, Stearamide MEA, Stearamide MEA-Stearate, Stearamide MIPA, PEG-2 Cocamide, PEG-3 Cocamide, PEG-4 Cocamide, PEG-5 Cocamide, PEG-6 Cocamide, PEG-7 Cocamide, PEG-3 Lauramide, PEG-5 Lauramide, PEG-3 Oleamide, PEG-9 Oleamide, PEG-4 Stearamide, PEG-10 Stearamide, PPG-2 Cocamide, PPG-2 Hydroxyethyl Cocamide, PPG-2 Hydroxyethyl Coco/Isostearamide, or mixtures thereof.

3. The hair styling composition of claim 1, wherein the hair styling composition includes one or more fatty alkanolamides.

4. The hair styling composition of claim 3, wherein the one or more fatty alkanolamides are selected from cocamide MEA, cocamide DEA, soyamide DEA, lauramide DEA, oleamide MIPA, stearamide MEA, myristamide DEA, stearamide DEA, oleylamide DEA, tallowamide DEA lauramide MIPA, tallowamide MEA, isostearamide DEA, isostearamide MEA, or mixtures thereof.

5. The hair styling composition of claim 1, wherein the one or more non-hydroxy substituted fatty acids is selected from oleic acid, lauric acid, palmitic acid, myristic acid, stearic acid, linoleic acid, behenic acid, capric acid, or mixtures thereof.

6. The hair styling composition of claim 1, wherein the one or more hydroxy-substituted fatty acids of (c) are selected from 12-hydroxystearic acid, 9,10-dihydroxyoctadecanoic acid, 9,10,18-trihydroxyoctadecanoic acid, lesquerolic acid, 15-hydroxyhexadecanoic acid, isoricinoleic acid, densipolic acid, 14-hydroxy-eicosa-cis-11-cis-17-dienoic acid, 2-hydroxyoleic acid, 2-hydroxylinoleic acid, 18-hydroxystearic acid, 15-hydroxylinoleic acid, or mixtures thereof.

7. The hair styling composition of claim 1, wherein the one or more low-polar oils are selected from natural oils.

8. The hair styling composition of claim 1, further comprising:
(e) one or more alkoxylated polyol esters.

9. The hair styling composition of claim 8, wherein the one or more alkoxylated polyol esters are selected from pegylated derivatives of propylene glycol oleate, propylene glycol caprylate/caprate, propylene glycol cocoate, propylene glycol stearate, or mixtures thereof.

10. The hair styling composition of claim 8, wherein the one or more alkoxylated polyol esters are selected from PEG-55 propylene glycol oleate, PEG-6 propylene glycol caprylate/caprate, PEG-8 propylene glycol cocoate, PEG-25 propylene glycol stearate, and PEG-120 propylene glycol stearate, or mixtures thereof.

11. The hair styling composition of claim 1 having a translucent or opaque appearance.

12. A hair styling composition comprising:
(a) about 3 to about 10 wt. % of one or more fatty alkanolamides selected from cocamide MEA, cocamide DEA, soyamide DEA, lauramide DEA, oleamide MIPA, stearamide MEA, myristamide DEA, stearamide DEA, oleylamide DEA, tallowamide DEA lauramide MIPA, tallowamide MEA, isostearamide DEA, isostearamide MEA, or mixtures thereof;
(b) about 2 to about 8 wt. % of one or more non-hydroxy substituted fatty acids selected from oleic acid, lauric acid, palmitic acid, myristic acid, stearic acid, linoleic acid, capric acid, behenic acid, or mixtures thereof;
(c) about 1 to about 8 wt. % of one or more hydroxy substituted fatty acids selected from 12-hydroxystearic acid, 9,10-dihydroxyoctadecanoic acid, 9,10,18-trihydroxyoctadecanoic acid, lesquerolic acid, 15-hydroxyhexadecanoic acid, isoricinoleic acid, densipolic acid, 14-hydroxy-eicosa-cis-11-cis-17-dienoic acid, 2-hydroxyoleic acid, 2-hydroxylinoleic acid, 18-hydroxystearic acid, 15-hydroxylinoleic acid, or mixtures thereof thereof;
(d) about 72 to about 90 wt. % of one or more natural oils;
(e) optionally, about 0.5 to about 10 wt. % of one or more alkoxylated polyol esters selected from pegylated derivatives of propylene glycol oleate, propylene glycol caprylate/caprate, propylene glycol cocoate, propylene glycol stearate, and a mixture thereof;
(f) optionally, about 0.1 to about 10 wt. % of one or more water-soluble organic solvents; and
(g) optionally, about 0.1 to about 8 wt. % of one or more miscellaneous ingredients;
wherein the composition comprises less than 2 wt. % of water, the composition exhibits non-Newtonian shear thinning behavior, the composition is a wax-like consistency until subjected to shear, and all weight percentages are based on a total weight of the composition.

13. A method for styling hair comprising applying the hair styling composition of claim 1 to the hair.

14. The method of claim 13, wherein the hair is styled without rinsing the hair styling composition from the hair before styling the hair.

15. The hair styling composition of claim 1, wherein the one or more hydroxy substituted fatty acids is 12-hydroxystearic acid.

16. The hair styling composition of claim 12, wherein the one or more hydroxy substituted fatty acids is 12-hydroxystearic acid.

17. The hair styling composition of claim 15, wherein the one or more non-hydroxy substituted fatty acids includes oleic acid.

18. The hair styling composition of claim 16, wherein the one or more non-hydroxy substituted fatty acids includes oleic acid.

19. A hair styling composition consisting of:
- (a) about 1 to about 15 wt. % of one or more fatty alkanolamides;
- (b) about 1 to about 10 wt. % of one or more non-hydroxy substituted fatty acids;
- (c) about 1 to about 8 wt. % of one or more hydroxy substituted fatty acids;
- (d) about 70 to about 95 wt. % of one or more natural oils;
- (e) optionally, about 0.5 to about 10 wt. % of one or more alkoxylated polyol esters;
- (f) optionally, about 0.1 to about 10 wt. % of one or more water-soluble organic solvents; and
- (g) optionally, about 0.1 to about 8 wt. % of one or more miscellaneous ingredients;
  - wherein the composition comprises less than 2 wt. % of water,
  - the composition exhibits non-Newtonian shear thinning behavior,
  - the composition is a wax-like consistency until subjected to shear, and
  - all weight percentages are based on a total weight of the composition.

* * * * *